(12) United States Patent
Babcock et al.

(10) Patent No.: US 8,453,494 B2
(45) Date of Patent: Jun. 4, 2013

(54) GAS DETECTOR THAT UTILIZES AN ELECTRIC FIELD TO ASSIST IN THE COLLECTION AND REMOVAL OF GAS MOLECULES

(75) Inventors: Jeffrey A. Babcock, Santa Clara, CA (US); Peter J. Hopper, San Jose, CA (US); Yuri Mirgorodski, Sunnyvale, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 379 days.

(21) Appl. No.: 12/880,464

(22) Filed: Sep. 13, 2010

(65) Prior Publication Data

US 2012/0060587 A1    Mar. 15, 2012

(51) Int. Cl.
*G01N 27/12*    (2006.01)

(52) U.S. Cl.
USPC .......................... 73/31.06; 73/31.05; 73/1.06

(58) Field of Classification Search
USPC ...................... 73/31.05, 31.06, 1.06
See application file for complete search history.

(56) References Cited

U.S. PATENT DOCUMENTS

2005/0235735 A1* 10/2005 Doll et al. .................... 73/31.06
2010/0323258 A1* 12/2010 Blackburn et al. ............ 429/428

* cited by examiner

*Primary Examiner* — Hezron E Williams
*Assistant Examiner* — Paul West
(74) *Attorney, Agent, or Firm* — Eugene C. Conser; Wade J. Brady, III; Frederick J. Telecky, Jr.

(57) ABSTRACT

A semiconductor-based gas detector enhances the collection of gas molecules and also provides a self-contained means for removing collected gas molecules by utilizing one or more electric fields to transport the gas molecules to and away from a metallic material that has a high permeability to the gas molecules.

13 Claims, 26 Drawing Sheets

GAS DETECTOR THAT UTILIZES AN ELECTRIC FIELD TO ASSIST IN THE COLLECTION AND REMOVAL OF GAS MOLECULES

BACKGROUND OF THE INVENTION

1. Field of the Invention

The present invention relates to a gas detector and, more particularly, to a gas detector that utilizes an electric field to assist in the collection and removal of gas molecules.

2. Description of the Related Art

A semiconductor-based gas detector is a device that is sensitive to the presence of a gas species. When a gas detector is exposed to a gas species, the gas detector collects gas molecules and then measures the number of collected gas molecules to determine the concentration of the gas species. Carbon diode and other gas species can be detected by a gas detector.

FIGS. 1A-1C show views that illustrate a first example of a conventional gas detector 100. FIG. 1A shows a plan view. FIG. 1B shows a cross-sectional view taken along line 1B-1B of FIG. 1A, while FIG. 1C shows a cross-sectional view taken along line 1C-1C of FIG. 1A. As shown in FIGS. 1A-1C, gas detector 100 includes a p− substrate 110, a shallow trench isolation region STI that is formed in substrate 110, and an NMOS transistor 114 that is formed in and on substrate 110.

NMOS transistor 114, in turn, includes spaced-apart source and drain regions 116 and 118 that are formed in substrate 110, and a channel region 120 of substrate 110 that lies between the source and drain regions 116 and 118. The source and drain regions 116 and 118, in turn, each include an n+ region and an NLDD region.

In addition, NMOS transistor 114 includes a gate dielectric layer 122 that touches the top surface of substrate 110 over channel region 120, a gate 124 that touches the top surface of gate dielectric layer 122 over channel region 120, and a side wall spacer 126 that touches the side wall of gate 124.

Gate 124 is implemented with a material that has a high permeability to the gas species to be detected. For example, lanthanum oxide, tin oxide, indium oxide, and zink oxide are materials which have a high permeability to carbon dioxide. Other materials are well known to have high permeabilities to other gas species.

As further shown in FIG. 1, gas detector 100 also includes a first dielectric layer 130 that touches the top surface of substrate 110, and a number of contacts 132 that extend through first dielectric layer 130. The contacts 132 make individual electrical connections to source region 116, drain region 118, gate 124, and a p+ region of substrate 110.

In addition, gas detector 100 includes a number of metal traces 134 that touch the top surface of first dielectric layer 130, and a second dielectric layer 136 that touches the top surface of first dielectric layer 130 and the metal traces 134. The metal traces 134 make electrical connections to the contacts 132. Gas detector 100 further includes a window opening 140 that extends through the first and second dielectric layers 130 and 136 to expose the top surface of gate 124.

In operation, gas detector 100 begins with a calibration step, which is performed in an environment that is known to be free of, or have an insignificant concentration of, the to-be-measured gas species. The calibration step is utilized to determine a bias voltage for gate 124, which is used in a subsequent measurement step.

Gas detector 100 can be calibrated by first applying ground to substrate 110 and source region 116, a VCC voltage to drain region 118, and an initial calibration voltage to gate 124.

Once the voltages have been applied, the magnitude of the source current is measured. The initial calibration voltage is selected to ensure that a sub-threshold current flows out of source region 116.

Following this, the calibration voltage is incrementally increased, and the magnitude of the source current is re-measured. The process of incrementally increasing the calibration voltage and re-measuring the magnitude of the source current is repeated a number of times until the magnitude of the source current increases substantially, indicating the turn on of NMOS transistor 114.

After the source current has increased substantially, the process of incrementally increasing the calibration voltage and re-measuring the magnitude of the source current ends. Next, a calibration voltage is selected to be the bias voltage from the calibration voltages which were used to generate the source currents. For example, the calibration voltage selected to be the bias voltage can be the calibration voltage which lies just below the turn on voltage of NMOS transistor 114.

Once the bias voltage for gate 124 has been selected, the calibration step ends and a collection step begins. The collection step begins, for example, by grounding p− substrate 110, source region 116, and drain region 118, and electrically floating the gate 124 for a predetermined period of time.

When gas detector 100 is exposed to the gas species, random gas molecules of the gas species enter window 140 and hit the exposed top surface of gate 124. When a gas molecule hits the exposed top surface of gate 124, the gas molecule can bounce away from, or stick to, the exposed top surface of gate 124.

Due to the high permeability of the material used to form gate 124, a number of gas molecules that stick to the exposed top surface of gate 124 are absorbed by gate 124. The gas molecules that stick to gate 124 and are absorbed into gate 124 change the work function of the material used to form gate 124 which, in turn, has the effect of placing a positive charge on gate 124.

After the predetermined period of time, the collection step ends and a measurement step begins to determine the number of gas molecules which have been collected. The measurement step begins, for example, by applying the VCC voltage to drain region 118, grounding substrate 110 and source region 116, and applying the bias voltage to gate 124.

The total charge on gate 124 is the combination of the bias voltage and the effective charge placed on gate 124 by the gas molecules. As a result, when gas molecules have been collected, the total charge on gate 124 is greater than the bias voltage which, in turn, causes the source current to be larger than when no gas molecules have been collected. Thus, by evaluating the increase in source current when compared to the source current associated with the bias voltage, the effective charge placed on gate 124 by the gas species can be determined or accurately estimated.

The concentration of the gas species that corresponds with the increase in source current or the effective charge placed on gate 124 can then be determined by referencing a look-up table, where the entries in the look-up table are experimentally determined from a series of increased source currents and known gas concentrations.

FIGS. 2A-2D show views that illustrate a second example of a conventional gas detector 200. FIG. 2A shows a plan view. FIG. 2B shows a cross-sectional view taken along line 2B-2B of FIG. 2A, while FIGS. 2C and 2D both show a cross-sectional view taken along line 2C-2C of FIG. 2A. Gas detector 200 is similar to gas detector 100 and, as a result, utilizes the same reference numerals to designate the structures which are common to both detectors.

As shown in FIGS. 2A-2D, gas detector 200 differs from gas detector 100 in that gas detector 200 eliminates window 140 and utilizes a floating gate structure 224 in place of gate 124. Floating gate structure 224, which is conductive and electrically isolated from all other conductive structures, includes a lower floating gate 230 that touches gate dielectric layer 122 and first dielectric layer 130, an upper floating gate 232 that touches second dielectric layer 136, and a vertical connection structure 234 that electrically connects upper floating gate 232 to lower floating gate 230, and extends through the first and second dielectric layers 130 and 136.

Lower floating gate 230 can be implemented with polysilicon, and upper floating gate 232 can be implemented with a conventional metal trace material that has no or a very low permeability to the gas species to be detected. The upper and lower portions of vertical conductive structure 234 can be implemented with a conventional via/contact material that has no or a very low permeability to the gas species to be detected, while the wider middle section of vertical conductive structure 234 can be implemented with a conventional metal trace material that has no or a very low permeability to the gas species to be detected.

Gas detector 200 also differs from gas detector 100 in that gas detector 200 has an inter-gate dielectric 240, such as oxide-nitride-oxide (ONO), that touches the top surface of lower floating gate 230, and a control gate 242 that touches inter-gate dielectric 240 and lies over a portion of the top surface of lower floating gate 230.

In addition, rather than a contact 132 making an electrical connection with gate 124, the contact 132 instead makes an electrical connection with control gate 242. (Rather than utilizing dielectric 240 and control gate 242 as shown in FIG. 2C, a heavily doped region 244 that touches gate dielectric 122 and lies below a portion of lower floating gate 230 can alternately be formed as the control gate as illustrated in FIG. 2D. Although not shown, a contact 132 makes an electrical connection to doped region 244.)

Gas detector 200 further differs from gas detector 100 in that gas detector 200 includes a third dielectric layer 250 that touches the top surface of second dielectric layer 136 and upper floating gate 232. Gas detector 200 additionally differs from gas detector 100 in that gas detector 200 includes a detection structure 252 that touches the top surface of third dielectric layer 250.

Detection structure 252, which is electrically isolated from all other conductive structures, is implemented with a material that has a high permeability to the gas species to be detected. For example, lanthanum oxide, tin oxide, indium oxide, and zink oxide are materials which have a high permeability to carbon dioxide. Other materials are well known to have high permeabilities to other gas species.

The operation of gas detector 200 begins by calibrating gas detector 200 to determine a bias voltage for control gate 242 (or doped region 244). Gas detector 200 can be calibrated in the same manner as gas detector 100, except that the source currents are measured in response to placing voltages on control gate 242 (or doped region 244). The voltages placed on control gate 242 (or doped region 244), in turn, are capacitively coupled to floating gate structure 224. Due to the capacitive coupling, the bias voltage selected for control gate 242 (or doped region 244) is slightly larger than the bias voltage selected for gate 124.

Once the bias voltage for control gate 242 (or doped region 244) has been selected, the calibration step ends and a collection step begins. The collection step begins, for example, by grounding p− substrate 110, source region 116, drain region 118, and control gate 224 (or doped region 244) for a predetermined period of time.

When gas detector 200 is exposed to the gas species, random gas molecules of the gas species hit the exposed surface of detection structure 252. When a gas molecule hits the exposed surface of detection structure 252, the gas molecule can bounce away from, or stick to, the exposed surface of detection structure 252.

Due to the high permeability of the material used to form detection structure 252, a number of gas molecules that stick to the exposed surface of detection structure 252 are absorbed by detection structure 252. The gas molecules that stick to detection structure 252 and are absorbed into detection structure 252 change the work function of the material used to form detection structure 252 which, in turn, has the effect of placing a positive charge on detection structure 252.

After the predetermined period of time, the collection step ends and a measurement step begins to determine the number of gas molecules which have been collected. The measurement step begins, for example, by applying the VCC voltage to drain region 118, grounding p− substrate 110 and source region 116, and applying the bias voltage to control gate 224 (or doped region 244).

The total potential on floating gate structure 224 is defined by the voltage on control gate 242 (or doped region 244) and the effective charge placed on detection structure 252 by the gas molecules, both of which are capacitively coupled to floating gate structure 224. As a result, when gas molecules have been collected, the total potential on floating gate structure 224 is greater than the capacitively coupled potential of the bias voltage which, in turn, causes the source current to be larger than when no gas molecules have been collected. Thus, by evaluating the increase in source current when compared to the source current associated with the gate bias voltage, the effective charge placed on detection structure 252 by the gas species can be determined or accurately estimated.

The concentration of the gas species that corresponds with the increase in source current or the effective charge placed on detection structure 252 can then be determined by referencing a look-up table, where the entries in the look-up table are experimentally determined from a series of increased source currents and known gas concentrations.

One of the advantages of gas detector 200 over gas detector 100 is that third dielectric layer 250 provides an environmental barrier to the components that lie below third dielectric layer 250. By forming third dielectric layer 250 to be relatively thin, most of the effective charge placed on detection structure 252 can be capacitively coupled to floating gate structure 224.

In addition to using a transistor-based gas detector, resistor-based gas detectors can alternately be used. This is because in addition to effectively adding a positive charge to a material, gas molecules that stick to and are absorbed by a high permeability material also change the conductivity of the material.

FIGS. 3A-3C show views that illustrate a third example of a conventional gas detector 300. FIG. 3A shows a plan view. FIG. 3B shows a cross-sectional view taken along line 3B-3B of FIG. 3A, while FIG. 3C shows a cross-sectional view taken along line 3C-3C of FIG. 3A. Gas detector 300 is similar to gas detector 100 and, as a result, utilizes the same reference numerals to designate the structures which are common to both detectors.

As shown in FIGS. 3A-3C, gas detector 300 differs from gas detector 100 in that gas detector 300 utilizes a resistive structure 310 in lieu of gate 124, and a dielectric layer 312 in lieu of dielectric layer 122. Gas detector 300 also differs from gas detector 100 in that gas detector 300 eliminates the source and drain regions 116 and 118, and utilizes the contacts 132 to make connections to opposite sides of resistive structure 310. Resistive structure 310 can be identical to gate 124, while dielectric layer 312 can be thicker than gate dielectric layer 122.

Gas detector 300 can be calibrated by grounding substrate 110, applying a set of voltages to the opposite sides of resistive structure 310, and then measuring a baseline current through resistive structure 310. Gas detector 300 can collect gas molecules by electrically floating resistive structure 310, and grounding p− substrate 110. During collection, gas molecules that stick to, and are absorbed by, resistive structure 310 change the conductivity of resistive structure 310.

Gas detector 300 can measure the number of collected gas molecules by grounding substrate 110, applying the set of voltages to the opposite sides of resistive structure 310, and then measuring a current through resistive structure 310. Thus, by evaluating the change in current through resistive structure 310, the number of gas molecules collected by resistive structure 310 can be determined or accurately estimated. The concentration of the gas species that corresponds with the change in current can then be determined by referencing a look-up table, where the entries in the look-up table are experimentally determined from a series of currents and known gas concentrations.

Although gas detectors 100, 200, and 300 can be utilized to detect a number of gas species, there is a need for additional structures for detecting the presence of a gas species.

BRIEF DESCRIPTION OF THE DRAWINGS

FIG. 1A is a plan view. FIG. 1B is a cross-sectional view taken along line 1B-1B of FIG. 1A, while FIG. 1C is a cross-sectional view taken along line 1C-1C of FIG. 1A.

FIG. 2A is a plan view. FIG. 2B is a cross-sectional view taken along line 2B-2B of FIG. 2A, while FIGS. 2C and 2D are cross-sectional view taken along line 2C-2C of FIG. 2A.

FIG. 3A is a plan view. FIG. 3B is a cross-sectional view taken along line 3B-3B of FIG. 3A, while FIG. 3C is a cross-sectional view taken along line 3C-3C of FIG. 3A.

FIG. 4A is a plan view. FIG. 4B is a cross-sectional view taken along line 4B-4B of FIG. 4A, while FIG. 4C is a cross-sectional view taken along line 4C-4C of FIG. 4A, FIG. 4D is a cross-sectional view taken along line 4D-4D of FIG. 4A, and FIG. 4E is a cross-sectional view taken along line 4C-4C of FIG. 4A.

FIG. 6A is a plan view. FIG. 6B is a cross-sectional view taken along line 6B-6B of FIG. 6A, while FIGS. 6C and 6D are cross-sectional views taken along line 6C-6C of FIG. 6A, FIG. 6E is a cross-sectional view taken along line 6E-6E of FIG. 6A, FIG. 6F is a cross-sectional view taken along line 6F-6F of FIG. 6A, and FIG. 6G is a cross-sectional view taken along line 6C-6C of FIG. 6A.

FIG. 7A is a plan view. FIG. 7B is a cross-sectional view taken along line 7B-7B of FIG. 7A, while FIGS. 7C and 7D are cross-sectional views taken along line 7C-7C of FIG. 7A, and FIG. 7E is a cross-sectional view taken along line 7E-7E of FIG. 7A.

FIG. 9A is a plan view. FIG. 9B is a cross-sectional view taken along line 9B-9B of FIG. 9A, while FIGS. 9C and 9D are cross-sectional views taken along line 9C-9C of FIG. 9A, and FIG. 9E is a cross-sectional view taken along line 9E-9E of FIG. 9A.

FIG. 10A is a plan view. FIG. 10B is a cross-sectional view taken along line 10B-10B of FIG. 10A, while FIG. 10C is a cross-sectional view taken along line 10C-10C of FIG. 10A.

DETAILED DESCRIPTION OF THE INVENTION

Figure 1A:
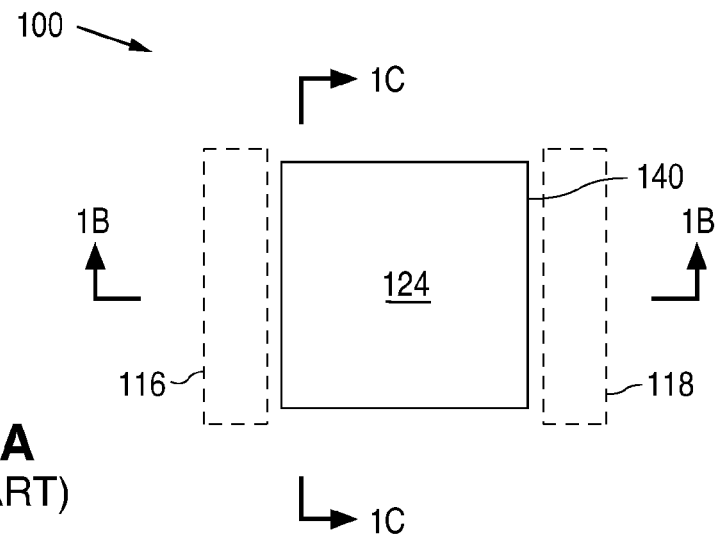
FIGS. 1A-1C are views illustrating a first example of a conventional gas detector 100.
Figure 1B:
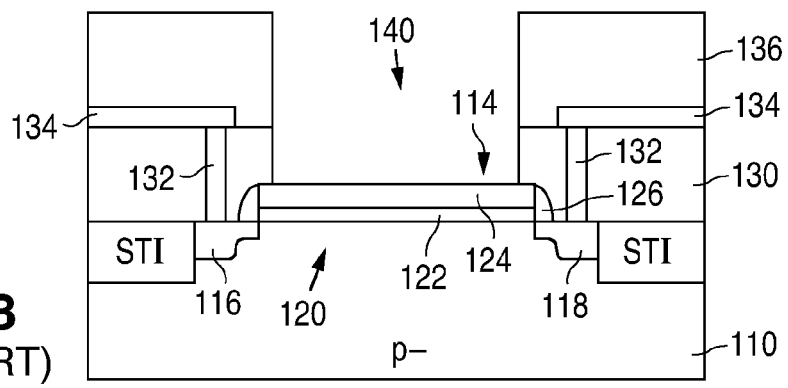
Figure 1C:
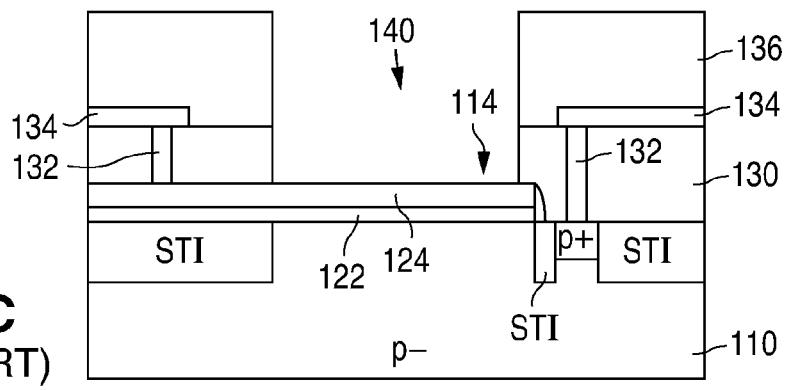
Figure 2A:
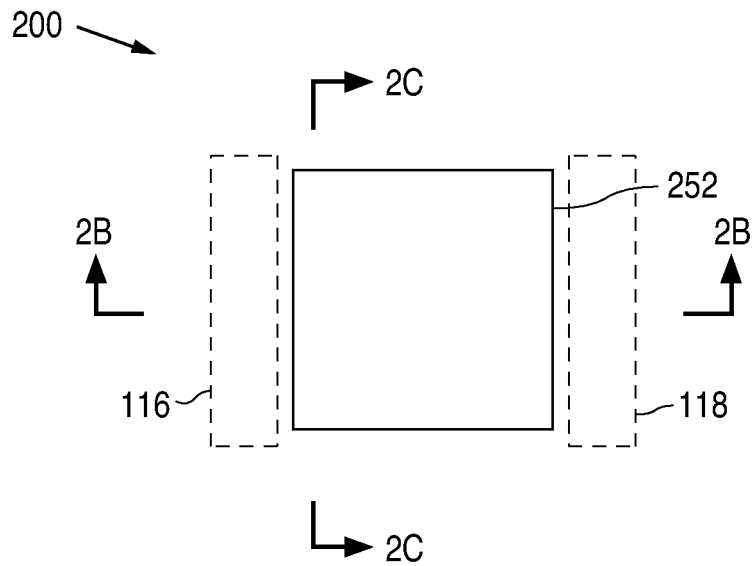
FIGS. 2A-2D are views illustrating a second example of a conventional gas detector 200.
Figure 2B:
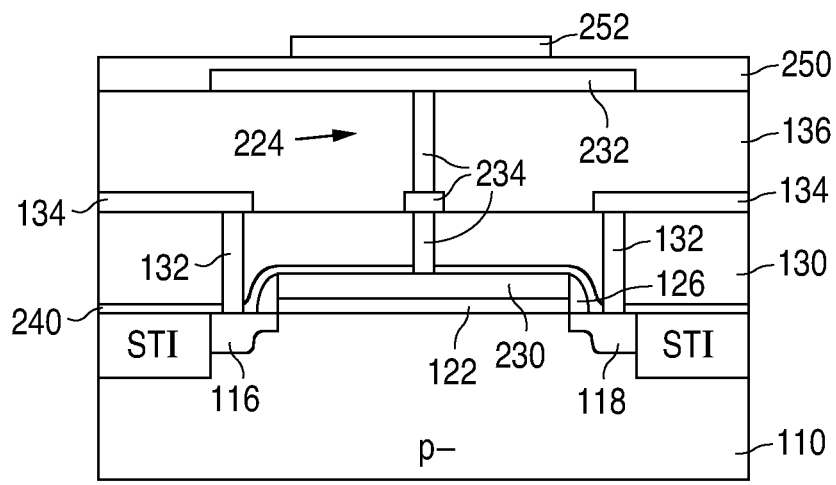
Figure 2C:
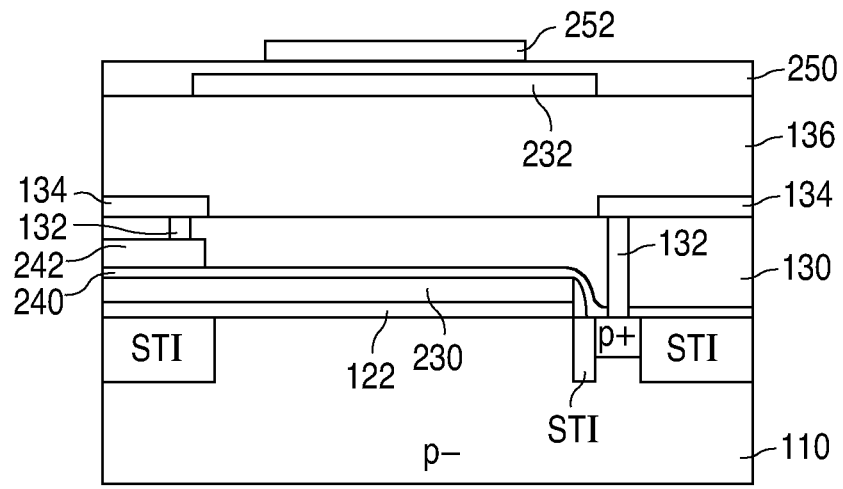
Figure 2D:
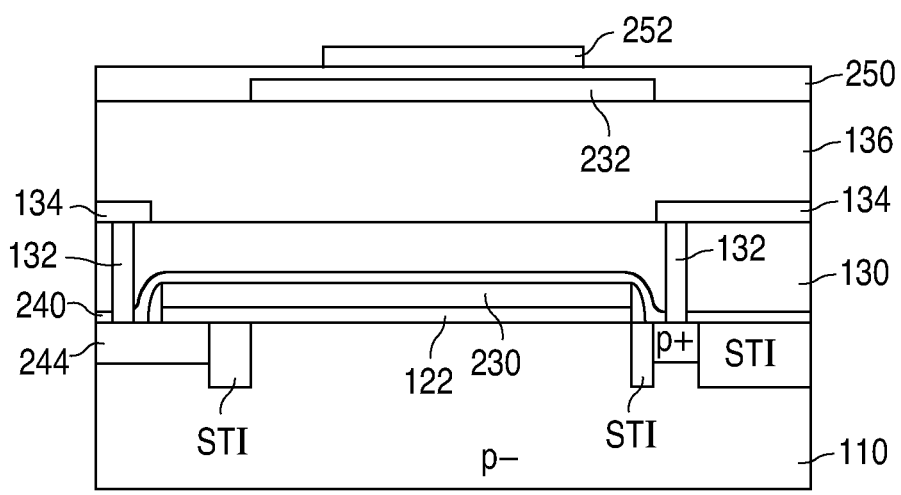
Figure 3A:
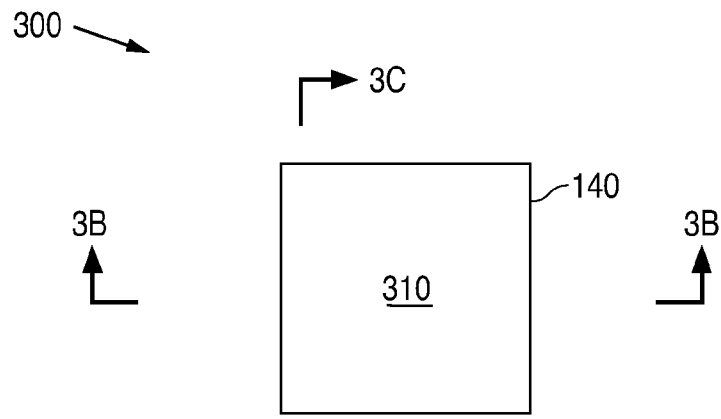
FIGS. 3A-3C are views illustrating a third example of a conventional gas detector 300.
Figure 3B:
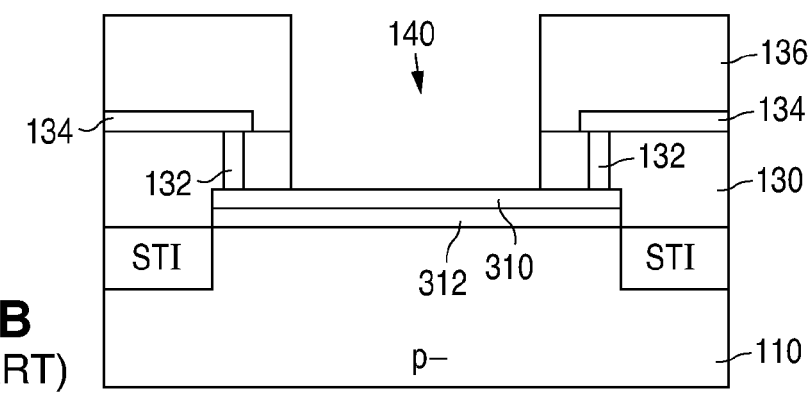
Figure 3C:
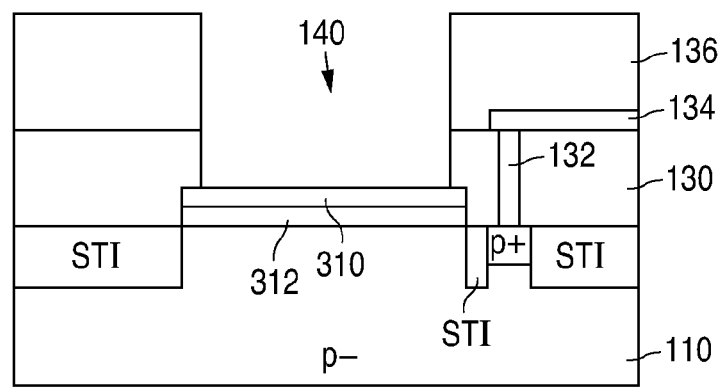
Figure 4A:
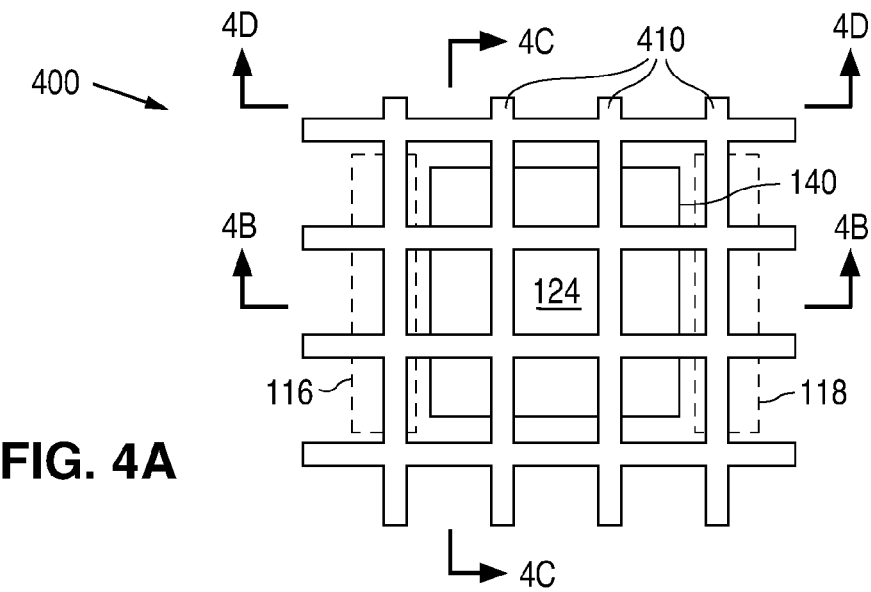
FIGS. 4A-4E are views illustrating an example of a gas detector 400 in accordance with the present invention.
Figure 4B:
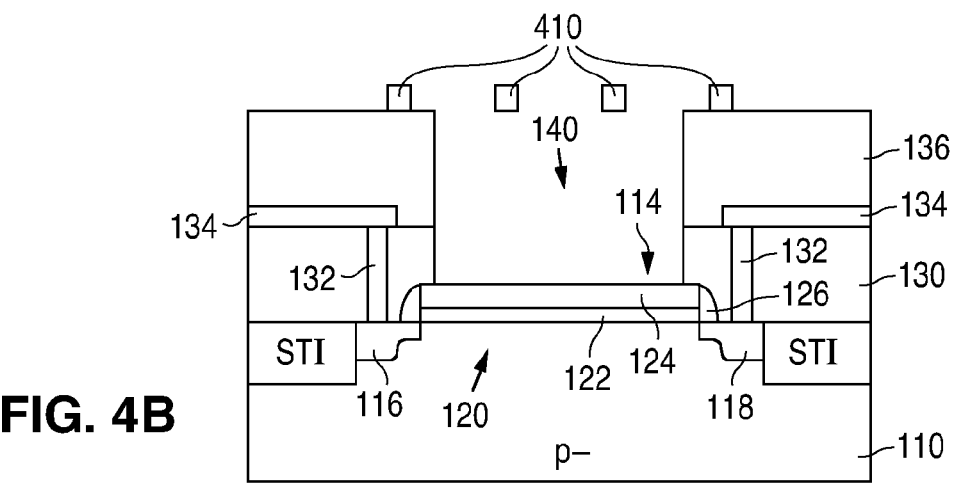
Figure 4C:
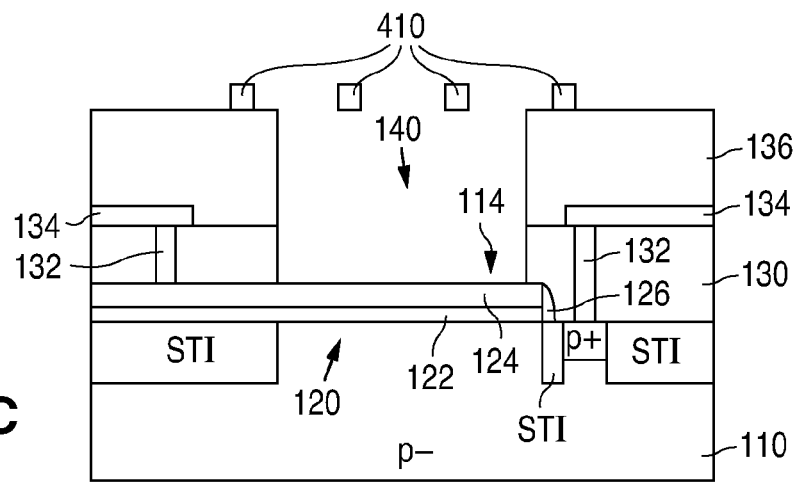
Figure 4D:
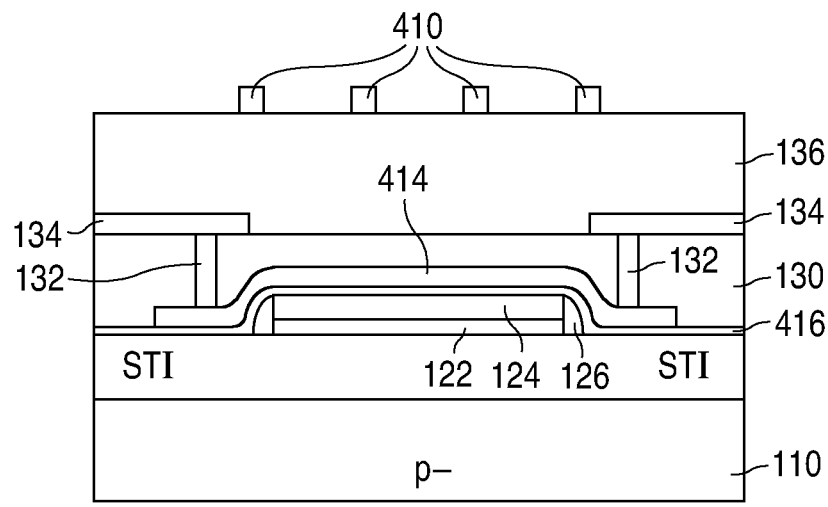
Figure 4E:
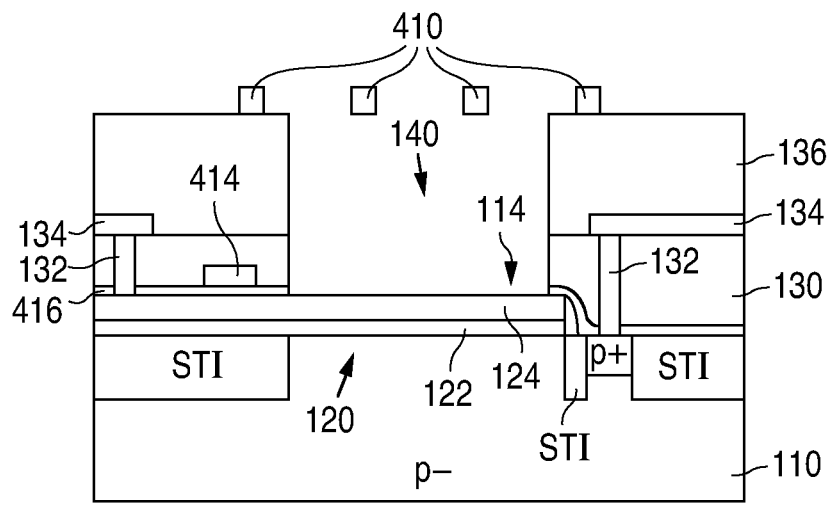

FIGS. 4A-4E show views that illustrate an example of a gas detector 400 in accordance with the present invention. FIG. 4A shows a plan view. FIG. 4B shows a cross-sectional view taken along line 4B-4B of FIG. 4A, while FIG. 4C shows a cross-sectional view taken along line 4C-4C of FIG. 4A, FIG. 4D shows a cross-sectional view taken along line 4D-4D of FIG. 4A, and FIG. 4E shows a cross-sectional view taken along line 4C-4C of FIG. 4A. Gas detector 400 is similar to gas detector 100 and, as a result, utilizes the same reference numerals to designate the structures which are common to both detectors.

As shown in FIGS. 4A-4C, gas detector 400 differs from gas detector 100 in that gas detector 400 includes a metal grid 410 that touches the top surface of second dielectric layer 136 and lies over window opening 140. Metal grid 410 can be implemented with a conventional metal trace material that has no or a very low permeability to the gas species to be detected.

Optionally, metal grid 410 can be implemented with a catalyzing metal, such as platinum or palladium. When metal grid 410 is implemented with a catalyzing metal, the catalyzing metal grid 410 can function as a reduction catalyst or an oxidization catalyst. For example, a catalyzing metal grid 410 can oxidize carbon monoxide to form carbon dioxide.

Figure 5:
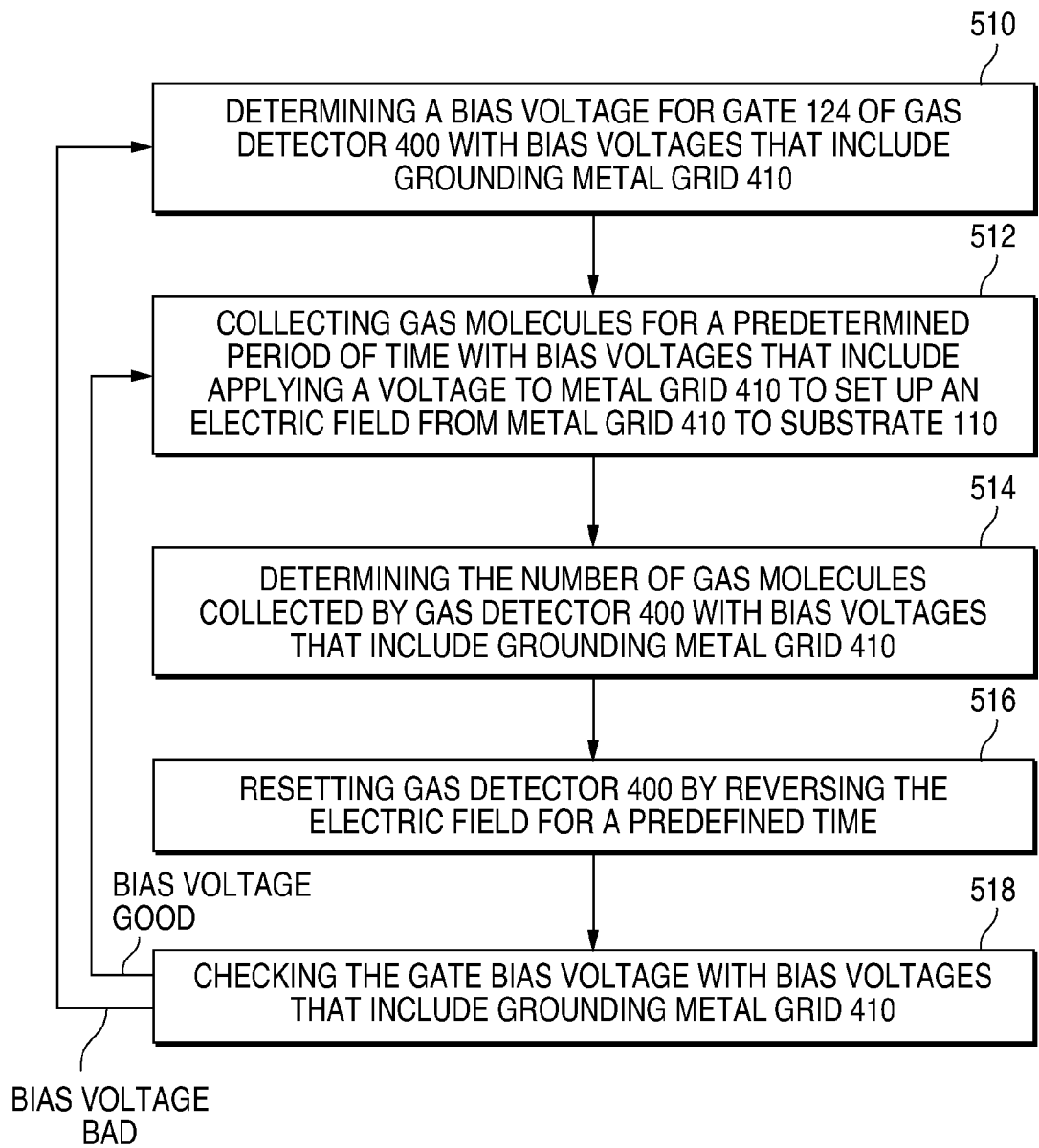
FIG. 5 is a flow chart illustrating an example of a method of operating gas detector 400 in accordance with the present invention.

FIG. 5 shows a flow chart that illustrates an example of a method of operating gas detector 400 in accordance with the present invention. As shown in FIG. 5, the method begins with a calibration step in 510 that determines a bias voltage for gate 124 of gas detector 400. Gas detector 400 can be calibrated using the same bias voltages and method as gas detector 100, except that metal grid 410 is grounded during the calibration step.

Once the bias voltage for gate 124 has been determined, the method moves to a collection step in 512 to collect gas molecules for a predetermined period of time. Gas detector 400 collects gas molecules in the same manner and with the same bias voltages as gas detector 100, except that a voltage is applied to metal grid 410 to set up an electric field from metal grid 410 to substrate 110.

For example, the electric field can be set up by applying a large positive voltage, such as 100V, to metal grid 410. The magnitude of the voltage, and thereby the magnitude of the electric field, is dependent upon the maximum electric field that gate dielectric layer 122 can withstand without breaking down or leaking.

In accordance with the present invention, the electric field significantly enhances the collection of gas molecules. The electric field that extends from metal grid 410 to substrate 110 transports polarized gas molecules and positively ionized gas molecules that enter window 140 down to gate 124. (The electric field also vertically aligns the polarized gas molecules.) Thus, rather than relying on the random motion of the gas molecules, the electric field transports the gas molecules directly to gate 124.

As noted above, when a gas molecule hits the top surface of gate 124, the gas molecule can bounce away from or stick to the top surface of gate 124. The electric field, however, improves the sticking coefficient of the gas molecules that hit the top surface of gate 124, thereby reducing the number of gas molecules that bounce off the top surface of gate 124 and escape from window 140.

This is because the energy required to bounce off the top surface of gate 124 and escape from window 140 must exceed the effect of the electric field. Thus, gas molecules which have sufficient energy to bounce off the top surface of gate 124, but lack sufficient energy to escape from window 140, will be again attracted to the top surface of gate 124 and eventually captured.

In addition, the electric field captures and re-directs a number of gas molecules that would normally escape from window 140 as a result of random collisions with other gas molecules, and transports these gas molecules down to gate 124. Further, when a gas molecule sticks to the top surface of gate 124, the electric field limits the surface movement of the molecule.

Due to the high permeability of the material used to form gate 124, a number of gas molecules that stick to the exposed top surface of gate 124 are absorbed by gate 124. The electric field also assists in the absorption of the gas molecules into gate 124. The gas molecules that stick to, and are absorbed into, gate 124 change the work function of the material used to form gate 124 which, in turn, has the effect of placing a positive charge on gate 124. Although to a lesser degree, the electric field is also expected to have the same effect on electrically neutral gas molecules. Experimental results have shown that water molecules, which are electrically neutral molecules, move under the influence of an electric field.

Some of the gas molecules that are absorbed into gate 124 migrate through gate 124 into gate dielectric layer 122 under the influence of the electric field. The vertical alignment of the polarized gas molecules and the positively ionized gas molecules in gate dielectric layer 122 have the effect of placing a positive charge in gate dielectric layer 122.

Returning again to FIG. 5, after the predetermined period of time has ended, the method moves to a measurement step in 514 to determine the number of gas molecules collected by gas detector 400. Gas detector 400 determines the number of collected gas molecules in the same manner and using the same bias voltages as gas detector 100, except that metal grid 410 is grounded during the measurement step.

Once the number of collected gas molecules has been determined, the method moves to an erase step in 516 to reset gas detector 400. Gas detector 400 is erased by reversing the electric field for a predefined time. For example, the electric field can be reversed by electrically floating the gate 124, grounding p– substrate 110, source region 116, and drain region 118, and applying a large negative voltage, such as −100V, to metal grid 410.

These bias conditions reverse the direction of the electric field which, in turn, pulls the gas molecules out of gate dielectric layer 122 and gate 124, and transports the gas molecules away from gate 124. Thus, in addition to significantly enhancing the collection of gas molecules, the present invention also erases gas detector 400.

After the predefined time, the method moves to a check step in 518 to check the bias voltage. The bias voltage is checked by applying the VCC voltage to drain region 118, grounding substrate 110, source region 116, and metal grid 410, and applying the bias voltage to gate 124. Following this, the source current is measured and compared to the source current associated with the original bias voltage.

When the source current is equal to or within an error tolerance of the source current associated with the original bias voltage, the method returns to the collection step in 512 to perform another test. On the other hand, when the source current is greater than the error tolerance, the method returns to the calibration step in 510 to determine a new bias voltage for gate 124. Thus, the check step in 518 allows the bias voltage to be adjusted to account for any gas molecules that were not removed from gate dielectric layer 122 and gate 124, thereby ensuring that the original sensitivity of gas detector 400 is maintained.

Optionally, as shown in FIGS. 4D and 4E, gas detector 400 can also include a heating element 414 that generates heat. Heating element 414, which is thermally coupled to gate 124, is utilized to increase the temperature of gate 124 during the collection and erasure steps, thereby increasing the ability of gate 124 to absorb gas molecules during the collection step, and discharge gas molecules during the erase step. Heating element 414, which lies over and is insulated from gate 124 by an isolation layer 416, has a pair of opposing ends that touch a pair of contacts 132.

In operation, heating element 414 generates heat when a current is passed through heating element 414 in response to a set of voltages applied to the opposite ends of heating element 414. Heating element 414, which lies below the lowest metal trace, can be implemented as a doped strip of polysilicon, single-crystal silicon, or other conductive material which generates heat when a current is passed through heating element 414.

Figure 6A:
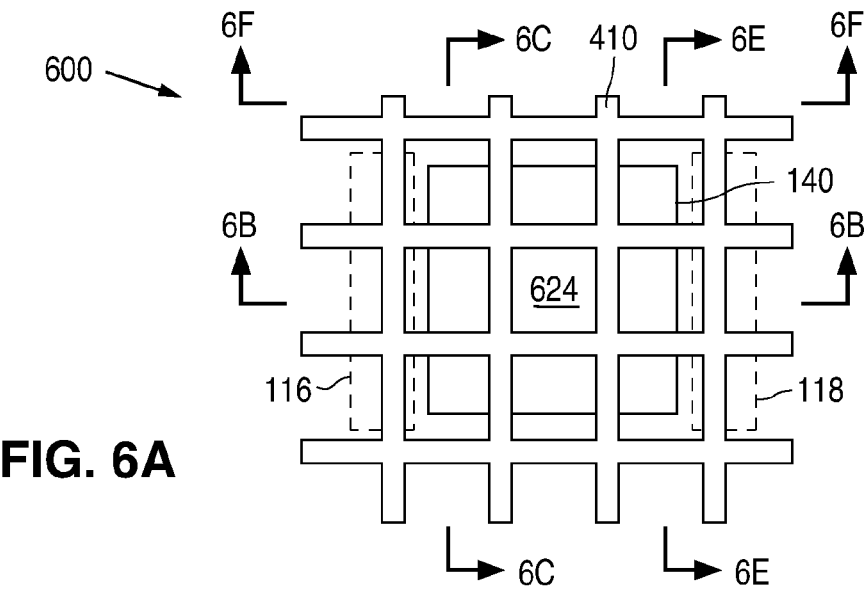
FIGS. 6A-6G are views illustrating an example of a gas detector 600 in accordance with an alternate embodiment of the present invention.
Figure 6B:
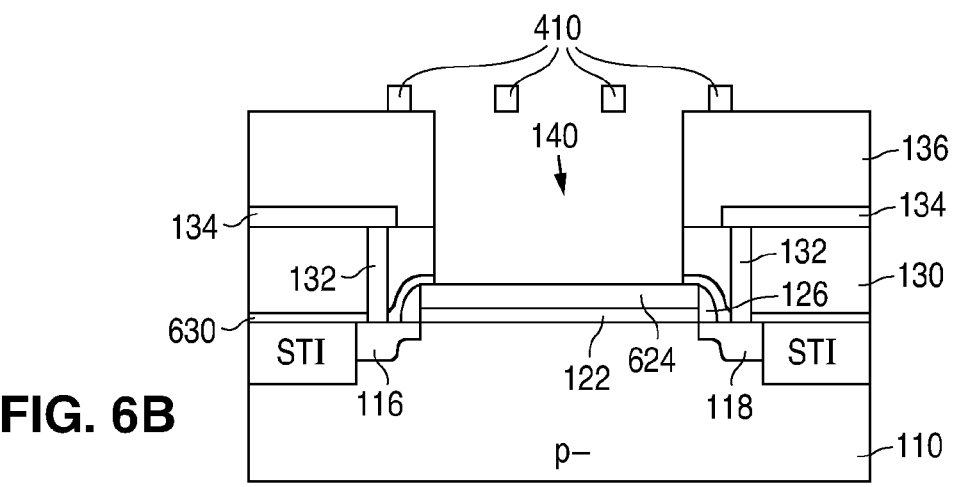
Figure 6C:
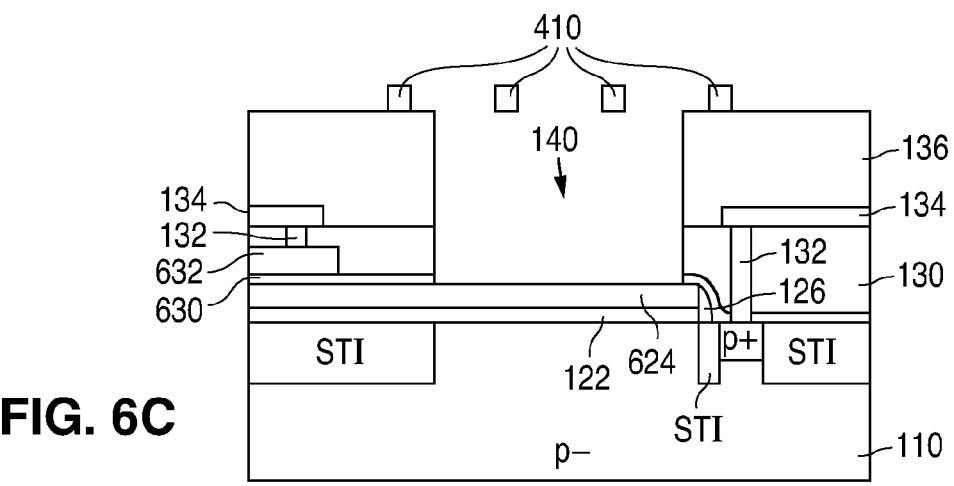
Figure 6D:
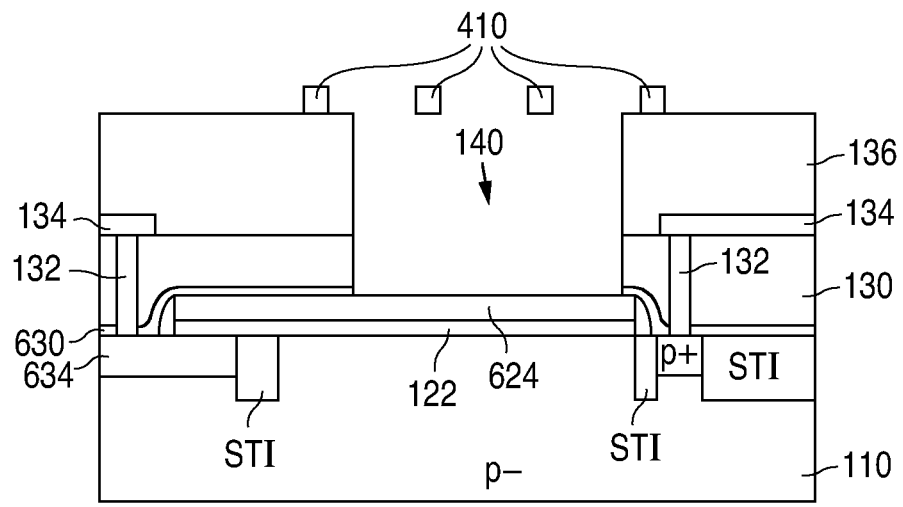
Figure 6E:
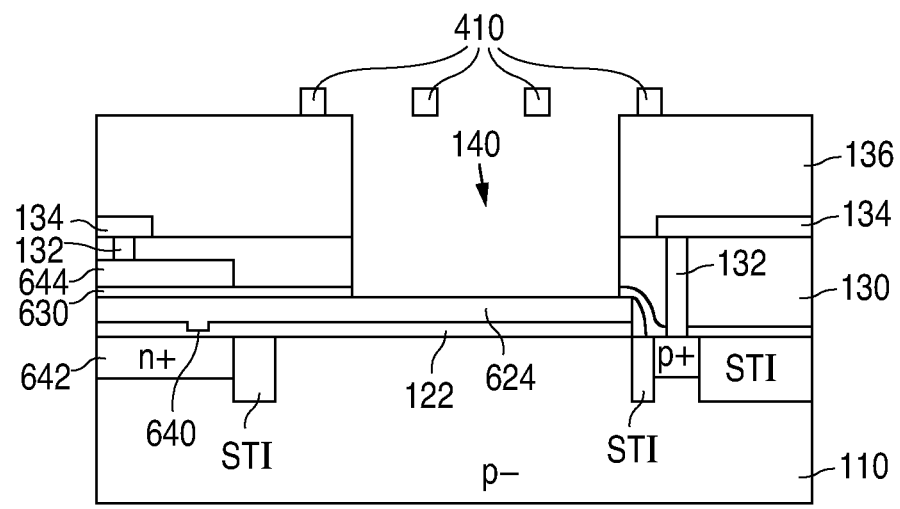
Figure 6F:
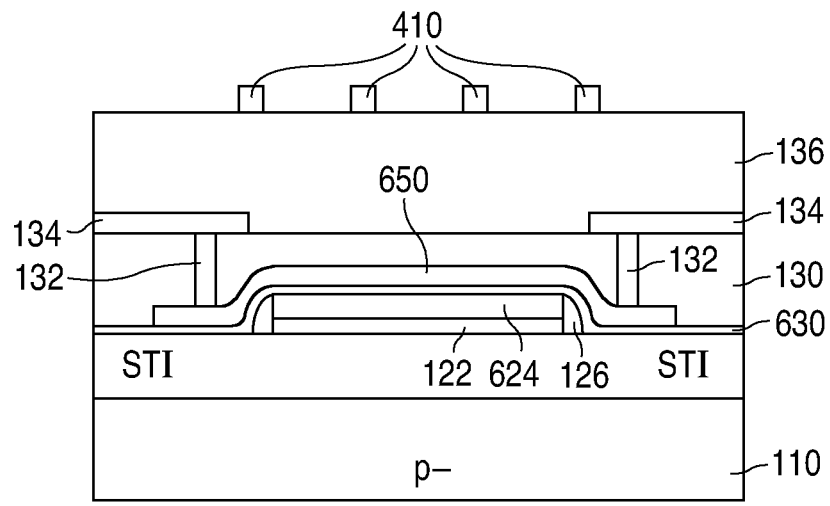
Figure 6G:
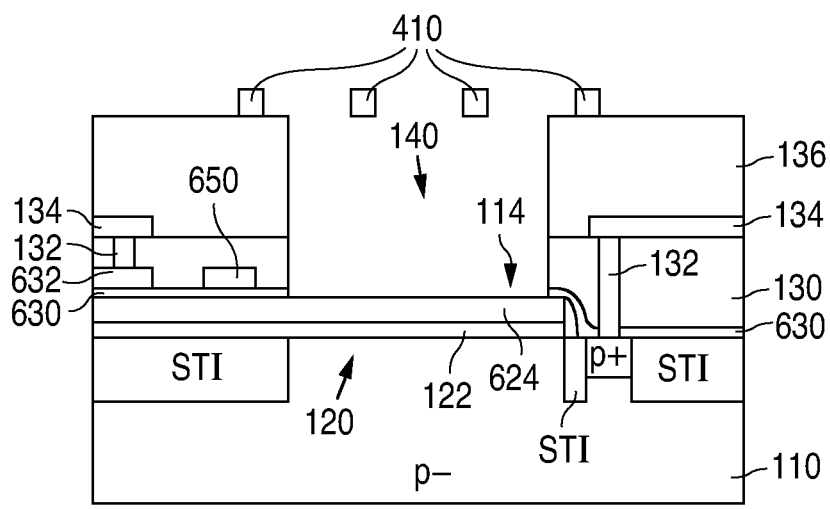

FIGS. 6A-6G show views that illustrate an example of a gas detector 600 in accordance with an alternate embodiment of the present invention. FIG. 6A shows a plan view. FIG. 6B shows a cross-sectional view taken along line 6B-6B of FIG. 6A, while FIGS. 6C and 6D both show a cross-sectional view taken along line 6C-6C of FIG. 6A, FIG. 6E shows a cross-sectional view taken along line 6E-6E of FIG. 6A, FIG. 6F shows a cross-sectional view taken along line 6F-6F of FIG. 6A, and FIG. 6G shows a cross-sectional view taken along line 6C-6C of FIG. 6A.

Gas detector 600 is similar to gas detector 400 and, as a result, utilizes the same reference numerals to designate the structures which are common to both detectors. As shown in FIGS. 6A-6C, gas detector 600 differs from gas detector 400 in that gas detector 600 utilizes a floating gate 624 in place of gate 124. Floating gate 624 is identical to gate 124 except that floating gate 624 is electrically isolated from all other conductive structures.

Gas detector 600 also differs from gas detector 400 in that gas detector 600 includes an inter-gate dielectric 630, such as oxide-nitride-oxide (ONO), that touches a portion of the top surface of floating gate 624, and a control gate 632 that touches inter-gate dielectric 630 and lies over a portion of the top surface of floating gate 624.

In addition, rather than a contact 132 making an electrical connection with gate 124, the contact 132 instead makes an electrical connection with control gate 632. (Rather than utilizing dielectric 630 and control gate 632 as shown in FIG. 6C, a heavily doped region 634 that touches gate dielectric 122 and lies below a portion of floating gate 624 can alternately be formed as the control gate as illustrated in FIG. 6D. Although not shown, a contact 132 makes an electrical connection to doped region 634.)

Gas detector 600 operates the same as gas detector 400, except for the following differences. In the calibration step in 510, gas detector 600 can be calibrated in the same manner as gas detector 400, except that the source currents are measured in response to placing voltages on control gate 632 (or doped region 634). The voltages placed on control gate 632 (or doped region 634), in turn, are capacitively coupled to floating gate 624. Due to the capacitive coupling, the bias voltage selected for control gate 632 (or doped region 634) is slightly larger than the bias voltage selected for gate 124 of gas detector 400.

In the collection step in 512, gas detector 600 collects gas molecules in the same manner and using the same bias voltages as gas detector 400, except that control gate 632 (or doped region 634) is also grounded for the predetermined period of time. When gas detector 600 is exposed to the gas species, the gas molecules that enter window 140 are transported down to floating gate 624 by the electric field that extends from metal grid 410 to substrate 110. When a gas molecule hits the exposed surface of floating gate 624, the gas molecule can bounce away from, or stick to, the exposed surface of floating gate 624.

Due to the high permeability of the material used to form floating gate 624, a number of gas molecules that stick to the exposed surface of floating gate 624 are absorbed by floating gate 624. The electric field also assists in the absorption of the gas molecules into floating gate 624. The gas molecules that stick to floating gate 624 and are absorbed into floating gate 624 change the work function of the material used to form floating gate 624 which, in turn, has the effect of placing a positive charge on floating gate 624.

Some of the gas molecules that are absorbed into floating gate 624 migrate through floating gate 624 into gate dielectric layer 122 under the influence of the electric field. The vertical alignment of the polarized gas molecules and the positively ionized gas molecules in gate dielectric layer 122 have the effect of placing a positive charge in gate dielectric layer 122.

In the measurement step in 514, gas detector 600 determines the number of collected gas molecules in the same manner and using the same bias voltages as gas detector 400, except that the bias voltage for control gate 632 (or doped region 634) is applied to control gate 632 (or doped region 634). The total potential on floating gate 624 is defined by the voltage on control gate 632 (or doped region 634), which is capacitively coupled to floating gate 624, and the effective charge placed on floating gate 624 by the gas molecules.

As a result, when gas molecules have been collected, the total potential on floating gate 624 is greater than the capacitively coupled potential of the bias voltage which, in turn, causes the source current to be larger than when no gas molecules have been collected. Thus, by evaluating the increase in the source current when compared to the source current associated with the bias voltage, the effective charge placed on floating gate 624 by the gas species can be determined or accurately estimated.

The concentration of the gas species that corresponds with the increase in source current or the effective charge placed on floating gate 624 can then be determined by referencing a look-up table, where the entries in the look-up table are experimentally determined from a series of increased source currents and known gas concentrations.

In the erase step in 516, gas detector 600 is erased in the same manner and using the same bias voltages as gas detector 400, except that control gate 632 (or doped region 634) is also grounded for the predefined period of time. These bias conditions reverse the direction of the electric field which, in turn, pulls the gas molecules out of gate dielectric layer 122 and floating gate 624, and transports the gas molecules away from floating gate 624.

In the check step in 518, gas detector 600 checks the bias voltage for control gate 632 (or doped region 634) in the same manner and using the same bias voltages as gas detector 400, except that the bias voltage for control gate 632 (or doped region 634) is applied to control gate 632 (or doped region 634).

As shown in FIG. 6E, gas detector 600 can optionally include a notched region 640 in gate dielectric 122, a heavily doped region 642 that lies below notched region 640, and a programming gate 644 that touches inter-gate dielectric 630 and lies laterally adjacent to control gate 632 shown in FIG. 6C. (Although not shown, a contact 132 makes an electrical connection to doped region 642.)

Programming gate 644 allows charge to be placed on or removed from floating gate 624 in a conventional manner by way of Fowler-Nordheim tunneling. Thus, when the method returns to the calibration step in 510 to again determine the bias voltage for control gate 632 (or doped region 634), the bias voltage for control gate 632 (or doped region 634) can remain unchanged if charge is injected onto floating gate 624 by way of programming to account for any gas molecules that were not removed during the erasure step in 516.

As shown in FIGS. 6F and 6G, gas detector 600 can also optionally include a heating element 650 that generates heat. Heating element 650, which is thermally coupled to floating gate 624, is utilized to increase the temperature of floating gate 624 during the collection and erasure steps, thereby increasing the ability of floating gate 624 to absorb gas molecules during the collection step, and discharge gas molecules during the erase step. Heating element 650, which lies over and is insulated from floating gate 624 by inter-gate dielectric 630, has a pair of opposing ends that touch a pair of contacts 132.

In operation, heating element 650 generates heat when a current is passed through heating element 650 in response to a set of voltages applied to the opposite ends of heating element 650. Heating element 650, which lies below the lowest metal trace, can be implemented as a doped strip of polysilicon, single-crystal silicon, or other conductive material which generates heat when a current is passed through heating element 650, but is preferably implemented with the same material as control gate 632.

Figure 7A:
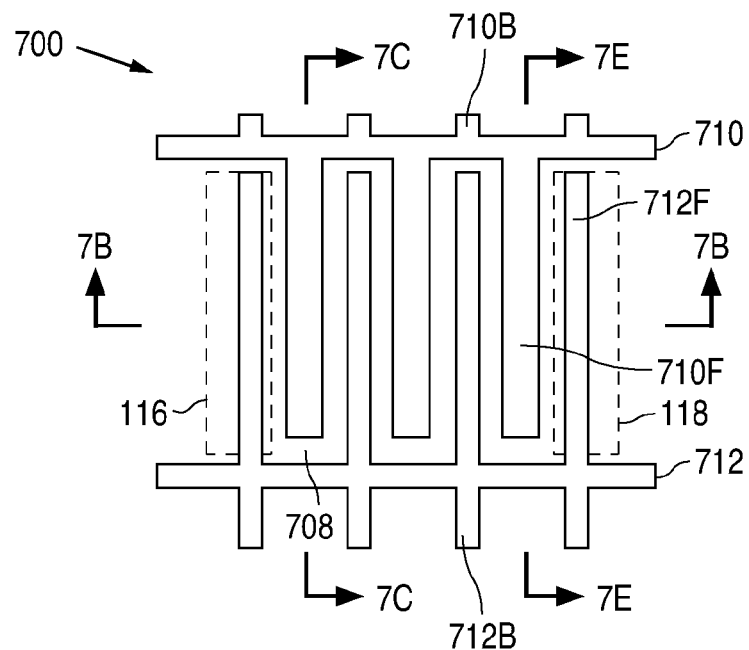
FIGS. 7A-7E are views illustrating an example of a gas detector 700 in accordance with an alternate embodiment of the present invention.
Figure 7B:
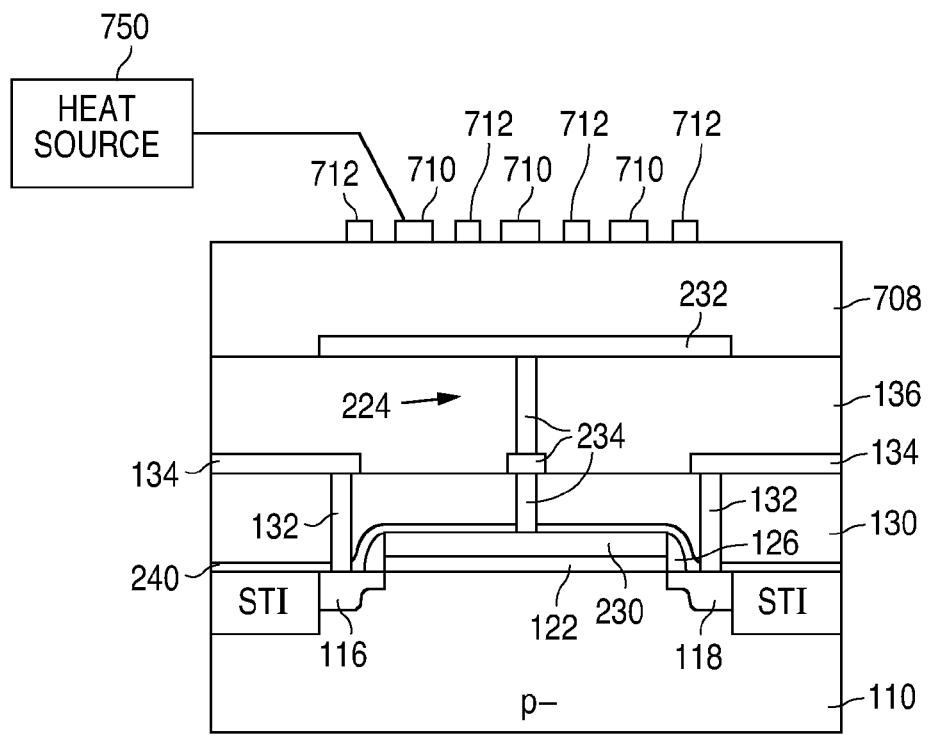
Figure 7C:
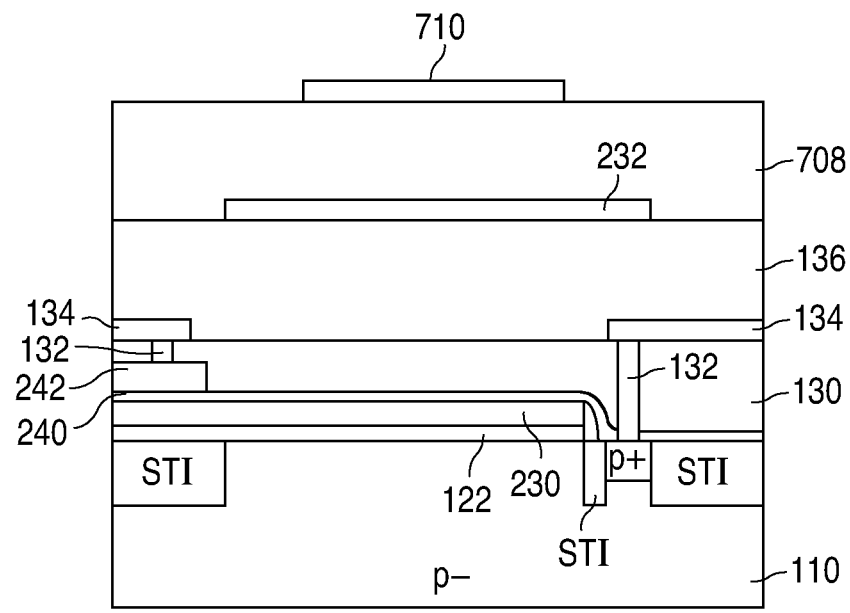
Figure 7D:
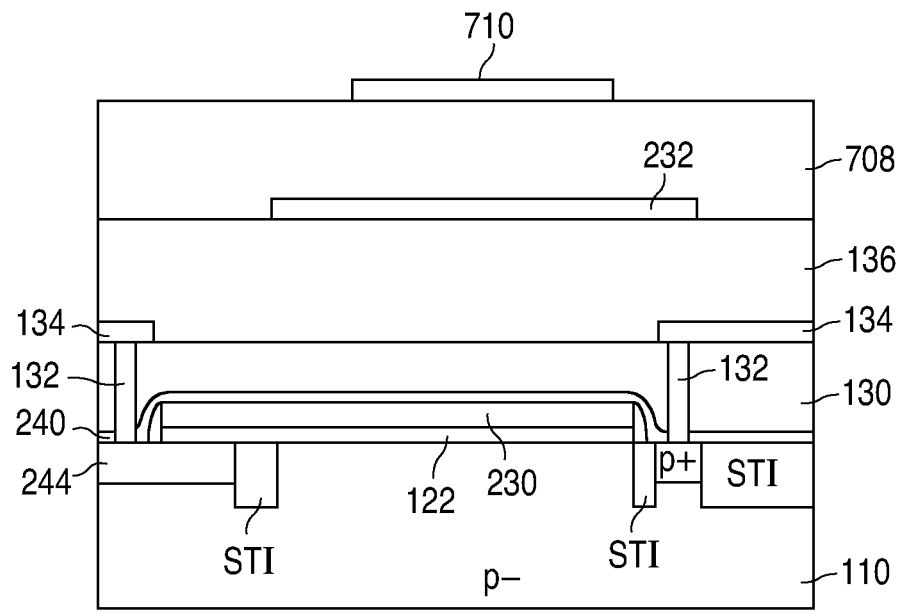
Figure 7E:
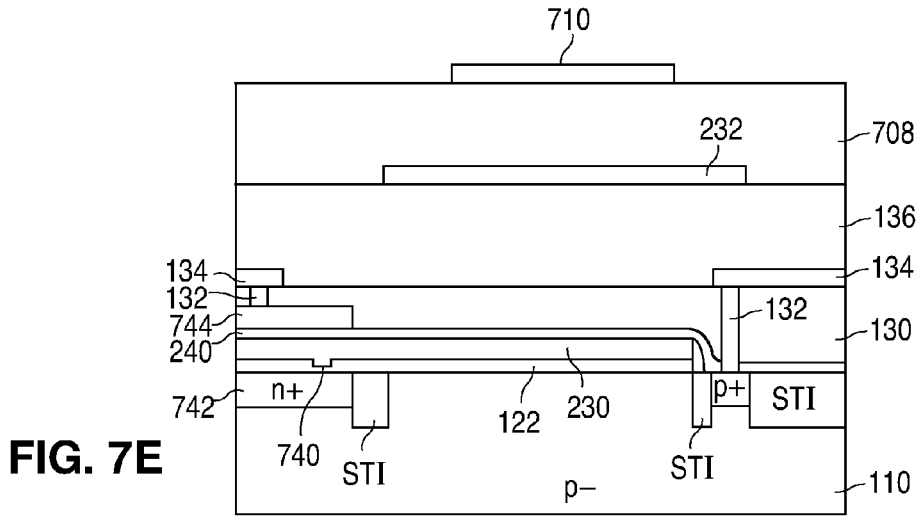

FIGS. 7A-7E show views that illustrate an example of a gas detector 700 in accordance with an alternate embodiment of the present invention. FIG. 7A shows a plan view. FIG. 7B shows a cross-sectional view taken along line 7B-7B of FIG. 7A, while FIGS. 7C and 7D show cross-sectional views taken along line 7C-7C of FIG. 7A, and FIG. 7E shows a cross-sectional view taken along line 7E-7E of FIG. 7A.

Gas detector 700 is similar to gas detector 200 and, as a result, utilizes the same reference numerals to designate the structures which are common to both detectors. As shown in FIGS. 7A-7D, gas detector 700 differs from gas detector 200 in that gas detector 700 utilizes a dielectric layer 708 in lieu of third dielectric layer 250, and a detection structure 710 in lieu of detection structure 252. Like detection structure 252, detection structure 710 is electrically isolated from all other conductive structures. In addition, gas detector 700 also includes a metal structure 712 that touches the top surface of dielectric layer 708.

Detection structure 710 has a base 710B and a number of fingers 710F that extend away from base 710B, while metal structure 712 also has a base 712B and a number of fingers 712F that extend away from base 712B. In addition, the fingers 710F of detection structure 710 and the fingers 712F of metal structure 712 are interdigitated so that the fingers 710F of detection structure 710 lie between the fingers 712F of metal structure 712. Further, the widths of the fingers 710F are wider than the widths of the fingers 712F.

Detection structure 710 and metal structure 712 are implemented with a material that has a high permeability to the gas species to be detected. For example, lanthanum oxide, tin oxide, indium oxide, and zink oxide are materials that have a high permeability to carbon dioxide. Other materials are well known to have permeabilities that are selective to other gas species. Optionally, metal structure 712 can be implemented with a conventional metal trace material that has no or a very low permeability to the gas species to be detected, or with a catalyzing metal, such as platinum or palladium.

Figure 8:
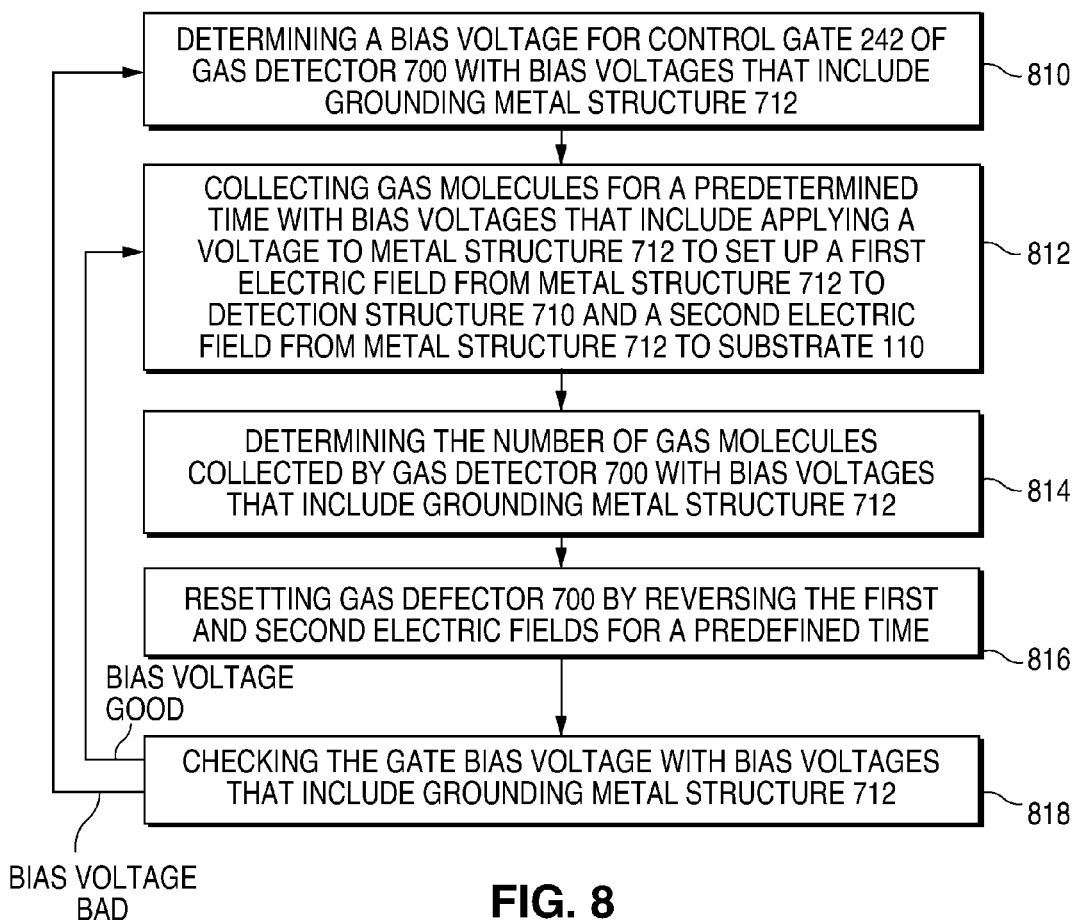
FIG. 8 is a flow chart illustrating an example of a method of operating gas detector 700 in accordance with the present invention.

FIG. 8 shows a flow chart that illustrates an example of a method of operating gas detector 700 in accordance with the present invention. As shown in FIG. 8, the method begins with a calibration step in 810 that determines a bias voltage for control gate 242 (or doped region 244). Gas detector 700 is calibrated in the same manner and using the same bias voltages as gas detector 200, except that metal structure 712 is grounded during the calibration step.

Once the bias voltage for control gate 242 (or doped region 244) has been determined, the method moves to a collection step in 812 to collect gas molecules for a predetermined time. Gas detector 700 collects gas molecules in the same manner and with the same bias voltages as gas detector 200, except that a voltage is applied to metal structure 712 during the collection step to set up a first electric field from metal structure 712 to detection structure 710, and a second electric field from metal structure 712 and detection structure 710 to substrate 110. Dielectric layer 708 is thicker than third dielectric layer 250 to accommodate the second electric field.

For example, the first and second electric fields can be set up by applying a large positive voltage, such as 100V, to metal structure 712. The large positive voltage placed on metal structure 712 is capacitively coupled to detection structure 710. Thus, when a large positive voltage is applied to metal structure 712, a smaller positive potential is present on detection structure 710 due to the capacitive coupling which, in turn, sets up the first electric field. In addition, the positive voltage on detection structure 710 and the positive potential on metal structure 712 set up the second electric field to extend from detection structure 710 and metal structure 712 to substrate 110.

In accordance with the present invention, the electric fields significantly enhance the collection of gas molecules. The first electric field transports polarized gas molecules and positively ionized gas molecules to the exposed surface of detection structure 710. When a gas molecule hits the exposed surface of detection structure 710, the gas molecule can bounce away from or stick to the exposed surface of detection structure 710. The first electric field, however, improves the sticking coefficient of the gas molecules that hit the exposed surface of detection structure 710, thereby reducing the number of gas molecules that bounce off the exposed surface of detection structure 710.

Due to the high permeability of the material used to form detection structure 710, a number of gas molecules that stick to the exposed surface of detection structure 710 are absorbed by detection structure 710. The first electric field also assists in the absorption of the gas molecules into detection structure 710. The gas molecules that stick to detection structure 710 and are absorbed into detection structure 710 change the work function of the material used to form detection structure 710 which, in turn, has the effect of placing a positive charge on detection structure 710.

Some of the gas molecules that are absorbed into detection structure 710 migrate through detection structure 710 into dielectric layer 708 under the influence of the second electric field. The vertical alignment of the polarized gas molecules and the positively ionized gas molecules in dielectric layer 708 have the effect of placing a positive charge in dielectric layer 708.

Thus, the first electric field transports polarized gas molecules and positively ionized gas molecules to the exposed surface of detection structure 710, improves the sticking coefficient of the gas molecules to detection structure 710, and assists in the absorption of the gas molecules into detection structure 710. In addition, the second electric field migrates the gas molecules through detection structure 710 and into dielectric layer 708.

Returning again to FIG. 8, after the predetermined period of time has ended, the method moves to a measurement step in 814 to determine the number of gas molecules collected by gas detector 700. Gas detector 700 determines the number of collected gas molecules in the same manner and using the same bias voltages as gas detector 200, except that metal structure 712 is grounded during the measurement step.

Once the number of collected gas molecules has been determined, the method moves to an erase step in 816 to reset gas detector 700. Gas detector 700 is erased by reversing the first and second electric fields for a predefined time. For example, the first and second electric fields can be reversed by grounding p− substrate 110, source region 116, drain region 118, and control gate 242 (or doped region 244), and placing a large negative voltage, such as −100V, on metal structure 712.

These bias conditions reverse the directions of the first and second electric fields which, in turn, pull the gas molecules out of dielectric layer 708 and detection structure 710 and transport the gas molecules away from detection structure 710. Thus, in addition to significantly enhancing the collection of gas molecules, the present invention also erases gas detector 700.

After the predefined time, the method moves to a check step in 818 to check the bias voltage for control gate 242 (or doped region 244). The bias voltage for control gate 242 (or doped region 244) is checked by applying the VCC voltage to drain region 118, grounding to p− substrate 110, source region 116, and metal structure 712, and applying the bias voltage to control gate 242 (or doped region 244). Following this, the source current is compared to the source current associated with the original bias voltage for control gate 242 (or doped region 244).

When the source current is equal to or within an error tolerance of the source current associated with the original bias voltage for control gate 242 (or doped region 244), the method returns to the collection step in 812 to perform another test. On the other hand, when the source current is greater than the error tolerance, the method returns to the calibration step in 810 to determine a new bias voltage for control gate 242 (or doped region 244). Thus, the check step in 818 allows the bias voltage for control gate 242 (or doped region 244) to be adjusted to account for any gas molecules that were not removed from dielectric layer 708 and detection structure 710, thereby ensuring that the original sensitivity of gas detector 700 is maintained.

As shown in FIG. 7E, gas detector 700 can optionally include a notched region 740 in gate dielectric layer 122, a heavily doped region 742 that lies below notched region 740, and a programming gate 744 that touches inter-gate dielectric 240 and lies laterally adjacent to control gate 242 in FIG. 7C. (Although not shown, a contact 132 makes an electrical connection to doped region 742.)

Programming gate 744 allows charge to be placed on or removed from floating gate structure 224 in a conventional manner by way of Fowler-Nordheim tunneling. Thus, when the method returns to the calibration step in 810 to again determine the bias voltage for control gate 242 (or doped region 244), the bias voltage for control gate 242 (or doped region 244) can remain unchanged if charge is injected onto floating gate structure 224 by way of programming to account for any gas molecules that were not removed during the erasure step in 816.

As further shown in FIG. 7B, gas detector 700 can optionally include an external heat source 750 that is thermally connected to detection structure 710. In operation, heat source 750 increases the temperature of detection structure 710 during the collection and erasure steps, thereby increasing the permeability of detection structure 710, and the ability of detection structure 710 to absorb gas molecules during the collection step, and discharge gas molecules during the erase step.

Figure 9A:
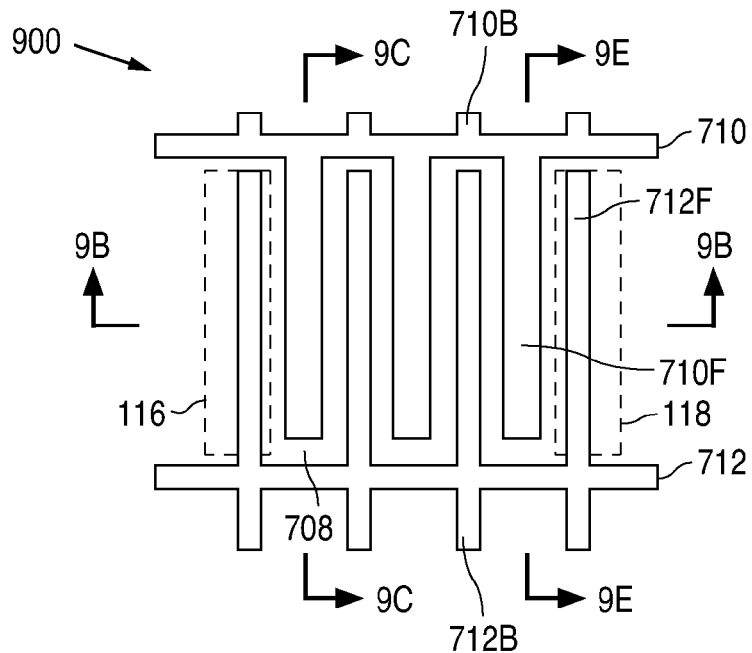
FIGS. 9A-9E are views illustrating an example of a gas detector 900 in accordance with an alternate embodiment of the present invention.
Figure 9B:
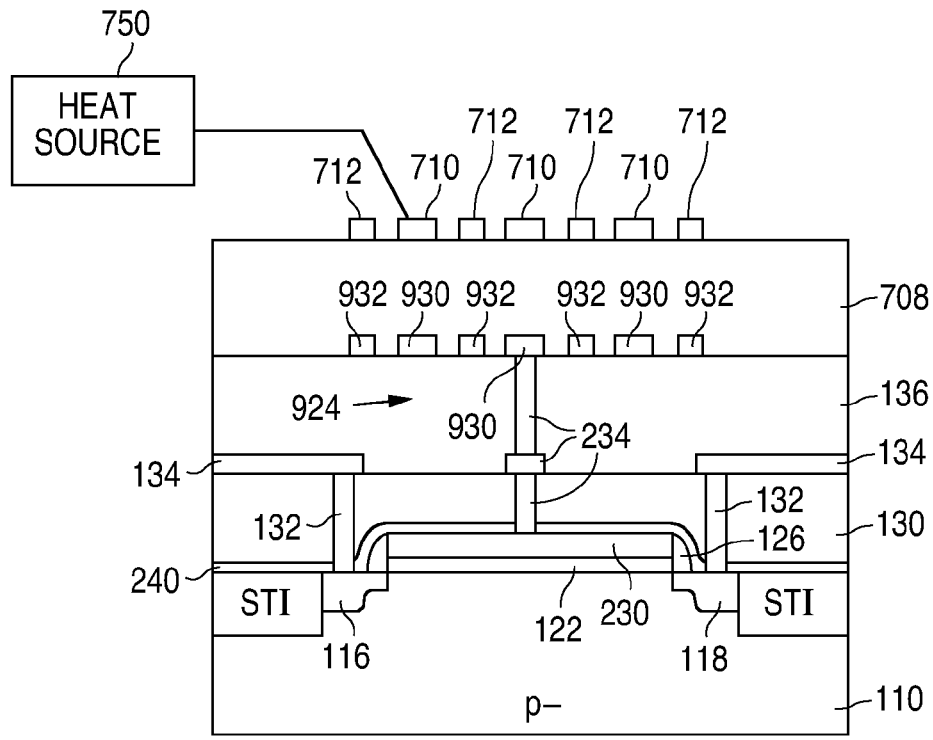
Figure 9C:
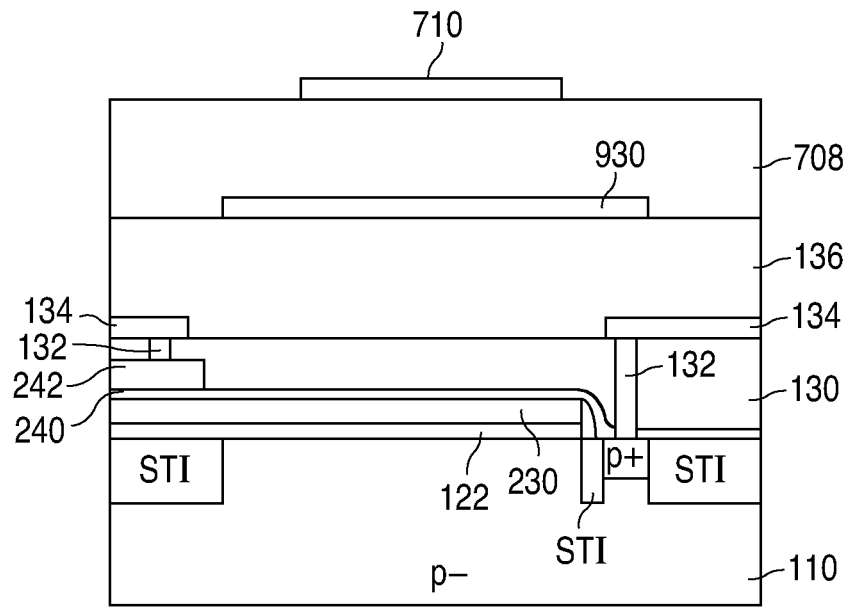
Figure 9D:
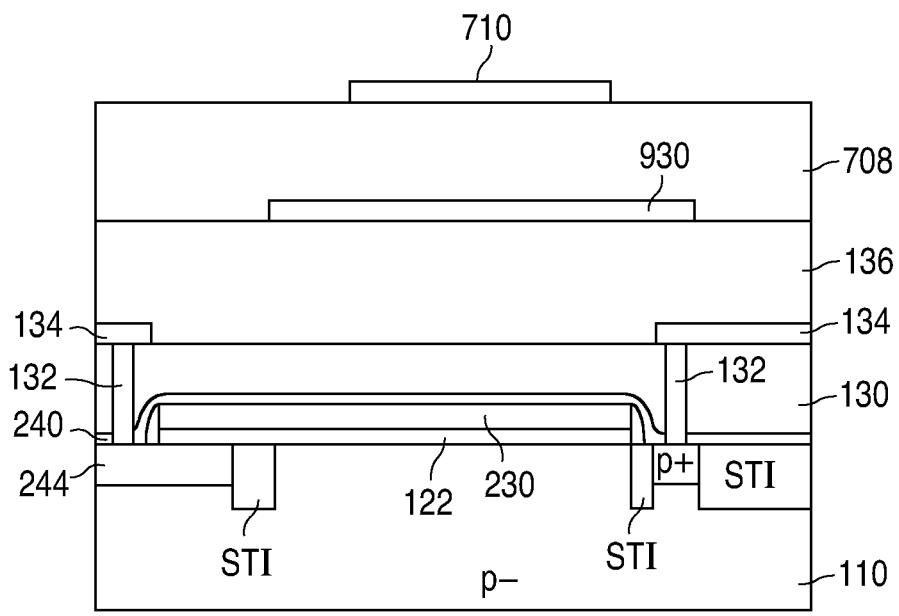
Figure 9E:
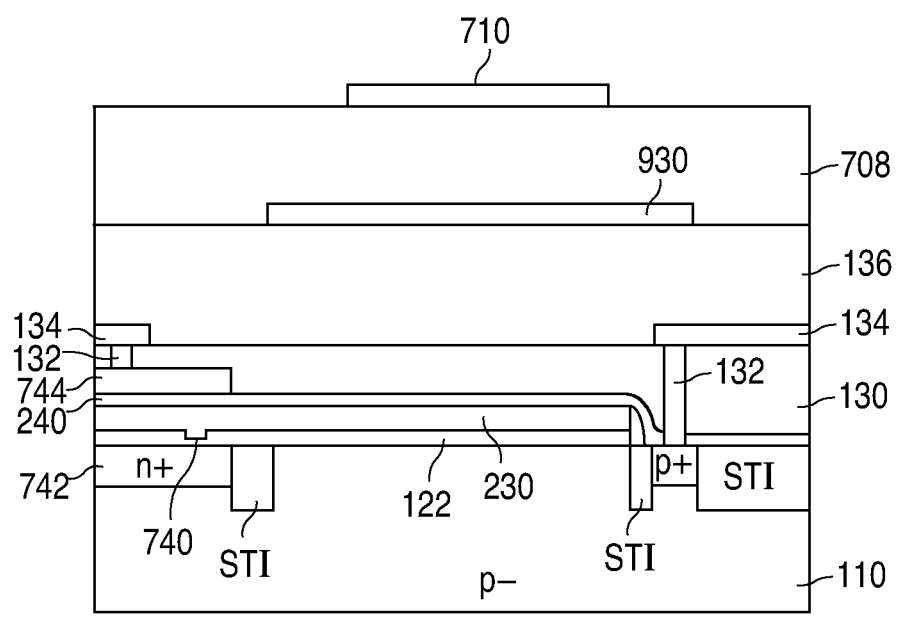

FIGS. 9A-9E show views that illustrate an example of a gas detector 900 in accordance with an alternate embodiment of the present invention. FIG. 9A shows a plan view. FIG. 9B shows a cross-sectional view taken along line 9B-9B of FIG. 9A, while FIGS. 9C and 9D show cross-sectional views taken along line 9C-9C of FIG. 9A, and FIG. 9E shows a cross-sectional view taken along line 9E-9E of FIG. 9A.

Gas detector 900 is similar to gas detector 700 and, as a result, utilizes the same reference numerals to designate the structures which are common to both detectors. As shown in FIGS. 9A-9E, gas detector 900 differs from gas detector 700 in that gas detector 900 utilizes a floating gate structure 924 in lieu of floating gate structure 224. Floating gate structure 924, in turn, differs from floating gate structure 224 in that a metal structure 930 is utilized in lieu of upper floating gate 232. Gas detector 900 also differs from gas detector 700 in that gas detector 900 includes a metal structure 932.

Metal structure 930 has an identical shape as detection structure 710, and lies directly below detection structure 710 between second dielectric layer 136 and dielectric layer 708. Similarly, metal structure 932 has an identical shape as metal structure 712, and lies directly below metal structure 712 between second dielectric layer 136 and dielectric layer 708. In addition, the metal structures 930 and 932 can be implemented with a conventional metal trace material that has no or a very low permeability to the gas species to be detected.

Gas detector 900 operates the same as gas detector 700, except for the following differences. During the calibration step in 810, gas detector 900 is calibrated in the same manner and using the same bias voltages as gas detector 700, except that both metal structures 712 and 932 are grounded during the calibration step.

During the collection step in 812, gas detector 900 collects gas molecules in the same manner and using the same bias voltages as gas detector 700, except that voltages are applied to metal structures 712 and 932 during the collection step to set up a first electric field from metal structure 712 to detection structure 710, a second electric field from metal structure 712 and detection structure 710 to floating gate structure 924 and metal structure 932, and a third electric field from metal structure 932 to floating gate structure 924.

For example, the first, second, and third electric fields can be set up by applying a negative voltage, such as −100V, to control gate 242, a positive voltage, such as 100V, to metal structure 932, and a positive voltage, such as 300V, to metal structure 712. (Other combinations of voltages on control gate 242, metal structure 712, and metal structure 932 can also be used to provide equivalent electric fields.) The positive voltage placed on metal structure 712 is capacitively coupled to detection structure 710. Thus, when a positive voltage is applied to metal structure 712, a smaller positive potential is present on detection structure 710 due to the capacitive coupling which, in turn, sets up the first electric field.

The negative voltage placed on control gate 242 and the positive voltage placed on metal structure 932 are both capacitively coupled to floating gate structure 924. The potential on floating gate structure 924 is the sum of these capacitively coupled values. Thus, for example, when −100V are applied to control gate 242 and 100V are applied to metal structure 932, the potential on floating gate structure 924 is approximately 0V. The 100V on metal structure 932 and the 0V on floating gate structure 924 then set up the third electric field to extend from metal structure 932 to floating gate structure 924.

In addition, the positive potential on detection structure 710, the positive voltage on metal structure 712, the potential on floating gate structure 924, and the positive voltage on metal structure 932 set up the second electric field to extend from detection structure 710 and metal structure 712 to floating gate structure 924 and metal structure 932. Thus, the second electric field of gas detector 900 can be significantly larger than the second electric field of gas detector 700.

In accordance with the present invention, the electric fields significantly enhance the collection of gas molecules. As with gas detector 700, the first electric field transports polarized gas molecules and positively ionized gas molecules to the exposed surface of detection structure 710. When a gas molecule hits the exposed surface of detection structure 710, the gas molecule can bounce away from or stick to the exposed surface of detection structure 710. The first electric field, however, improves the sticking coefficient of the gas molecules that hit the exposed surface of detection structure 710, thereby reducing the number of gas molecules that bounce off the exposed surface of detection structure 710.

Due to the high permeability of the material used to form detection structure 710, a number of gas molecules that stick to the exposed surface of detection structure 710 are absorbed by detection structure 710. The first electric field also assists in the absorption of the gas molecules into detection structure 710. The gas molecules that stick to detection structure 710 and are absorbed into detection structure 710 change the work function of the material used to form detection structure 710 which, in turn, has the effect of placing a positive charge on detection structure 710.

Some of the gas molecules that are absorbed into detection structure 710 migrate through detection structure 710 into dielectric layer 708 under the influence of the second electric field. However, because the second electric field in gas detector 900 can be much larger than the second electric field in gas detector 700, the number of gas molecules that migrate into dielectric layer 708 is greatly enhanced. The vertical alignment of the polarized gas molecules and the positively ionized gas molecules in dielectric layer 708 have the effect of placing a positive charge in dielectric layer 708. After migrating into dielectric layer 708, the third electric field migrates the gas molecules towards floating gate structure 924.

Thus, the first electric field transports polarized gas molecules and positively ionized gas molecules to the exposed surface of detection structure 710, improves the sticking coefficient of the gas molecules to detection structure 710, and assists in the absorption of the gas molecules into detection structure 710. In addition, the second electric field migrates the gas molecules into dielectric layer 708, while the third electric field migrates the gas molecules towards floating gate structure 924.

During the measurement step in 814, gas detector 900 determines the number of collected gas molecules in the same manner and using the same bias voltages as gas detector 700, except that metal structure 932 is also grounded. During the reset step in 816, gas detector 900 is reset in the same manner and using the same bias voltages as gas detector 700, except that the voltages placed on control gate 242, metal structure 712, and metal structure 932 are selected to reverse the first, second, and third electric fields, thereby pulling the gas molecules out of dielectric layer 708 and detection structure 710 and transporting the gas molecules away from detection structure 710. During the check step in 818, gas detector 900 determines if the control gate bias voltage needs to be reset in the same manner and using the same bias voltages as gas detector 700, except that metal structure 932 is also grounded.

Figure 10A:
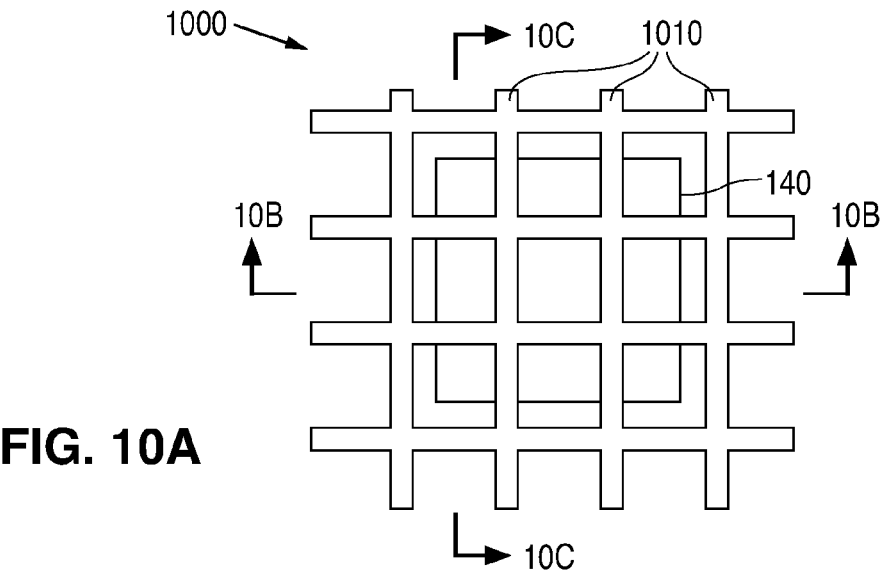
FIGS. 10A-10C are views illustrating an example of a gas detector 1000 in accordance with the present invention.
Figure 10B:
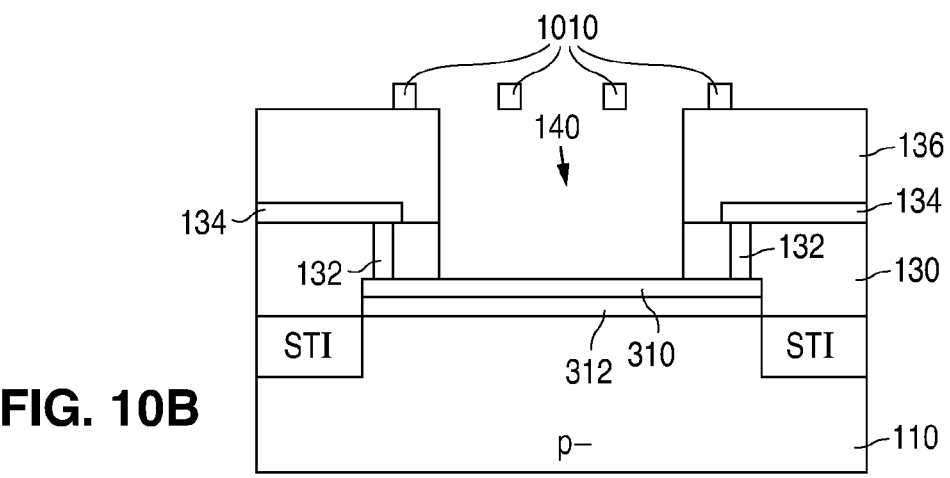
Figure 10C:
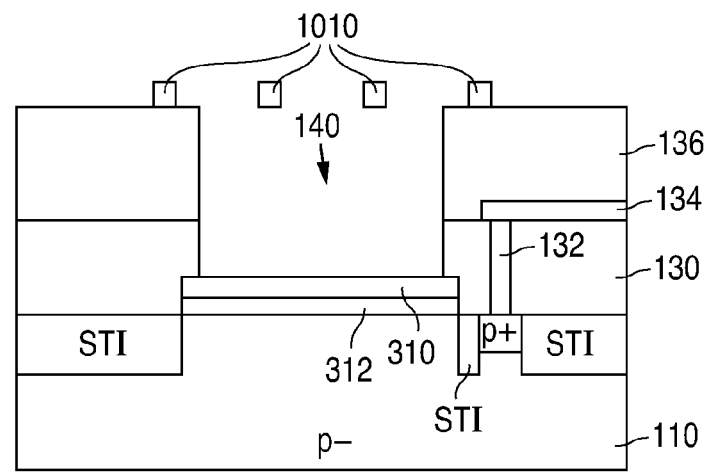

FIGS. 10A-10C show views that illustrate an example of a gas detector 1000 in accordance with the present invention. FIG. 10A shows a plan view. FIG. 10B shows a cross-sectional view taken along line 10B-10B of FIG. 10A, while FIG. 10C shows a cross-sectional view taken along line 10C-10C of FIG. 10A. Gas detector 1000 is similar to gas detector 300 and, as a result, utilizes the same reference numerals to designate the structures which are common to both detectors.

As shown in FIGS. 10A-10C, gas detector 1000 differs from gas detector 300 in that gas detector 1000 includes a metal grid 1010 that touches the top surface of second dielectric layer 136 and lies over window opening 140. Metal grid 1010 can be implemented with a conventional metal trace material that has no or a very low permeability to the gas species to be detected.

Optionally, metal grid 1010 can be implemented with a catalyzing metal, such as platinum or palladium. When metal grid 1010 is implemented with a catalyzing metal, the catalyzing metal grid 1010 can function as a reduction catalyst or an oxidization catalyst. For example, a catalyzing metal grid 1010 can oxidize carbon monoxide to form carbon dioxide.

Figure 11:
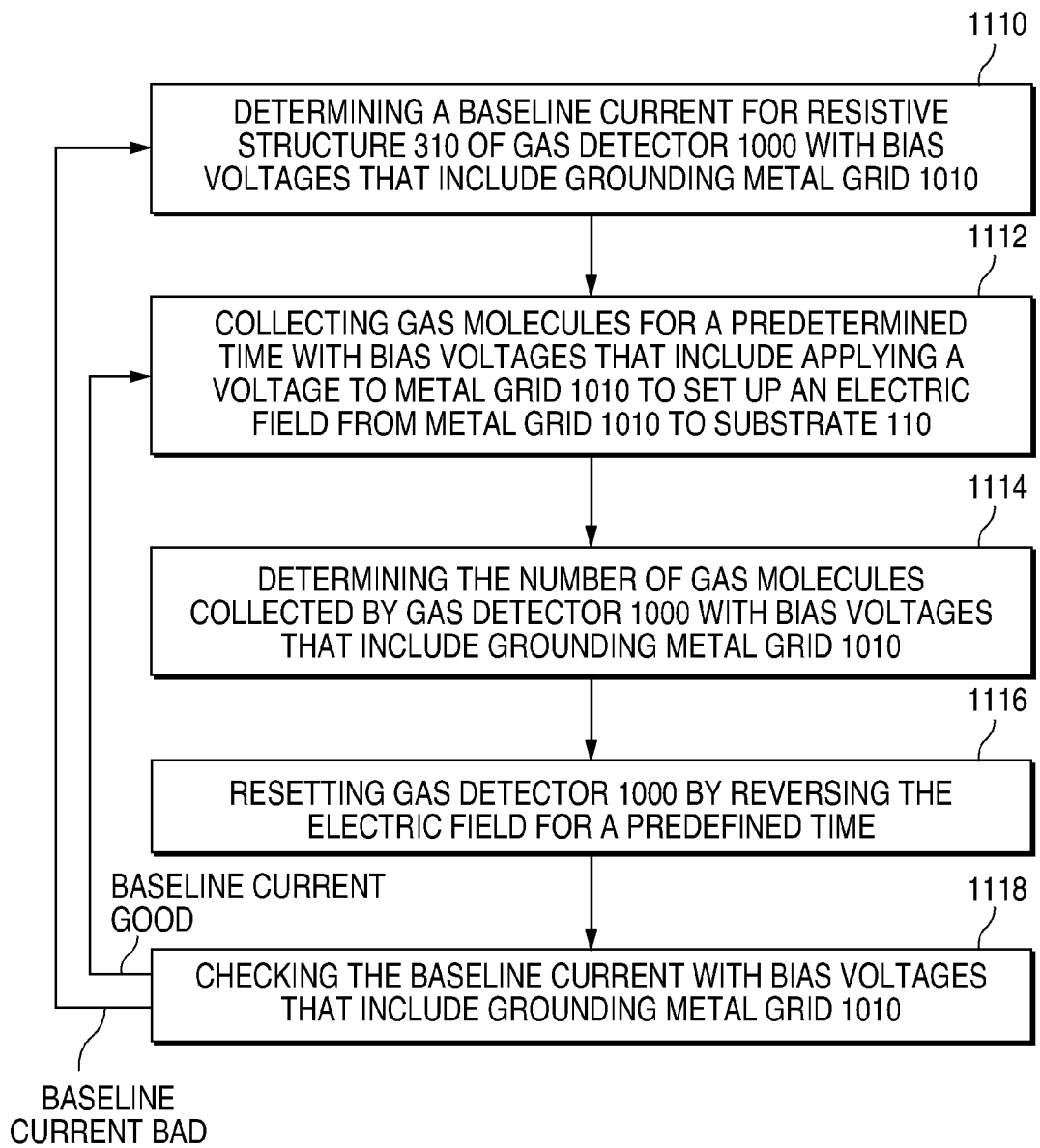
FIG. 11 is a flow chart illustrating an example of a method of operating gas detector 1000 in accordance with the present invention.

FIG. 11 shows a flow chart that illustrates an example of a method of operating gas detector 1000 in accordance with the present invention. As shown in FIG. 11, the method begins with a calibration step in 1110 that determines a baseline current for resistive structure 310. Gas detector 1000 is calibrated in the same manner and using the same bias voltages as gas detector 300, except that metal grid 1010 is grounded during the calibration step.

Once the baseline current has been determined, the method moves to a collection step in 1112 to collect gas molecules for a predetermined time. Gas detector 1000 collects gas molecules in the same manner and with the same bias voltages as gas detector 300, except that a large positive voltage, such as 100V, is applied to metal grid 1010 during the collection step to set up an electric field from metal grid 1010 to substrate 110.

In accordance with the present invention, the electric field significantly enhances the collection of gas molecules. The electric field transports polarized gas molecules and positively ionized gas molecules to the exposed surface of resistive structure 310. When a gas molecule hits the exposed surface of resistive structure 310, the gas molecule can bounce away from or stick to the exposed surface of resistive structure 310. The electric field, however, improves the sticking coefficient of the gas molecules that hit the exposed surface of resistive structure 310, thereby reducing the number of gas molecules that bounce off the exposed surface of resistive structure 310.

Due to the high permeability of the material used to form resistive structure 310, a number of gas molecules that stick to the exposed surface of resistive structure 310 are absorbed by resistive structure 310. The electric field also assists in the absorption of the gas molecules into resistive structure 310. The gas molecules that stick to resistive structure 310 and are absorbed into resistive structure 310 change the conductivity of the material used to form resistive structure 310.

Some of the gas molecules that are absorbed into resistive structure 310 migrate through resistive structure 310 into dielectric layer 312 under the influence of the electric field. These gas molecules, however, have no effect on the conductivity of resistive structure 310 and, therefore, can be ignored.

Returning again to FIG. 11, after the predetermined period of time has ended, the method moves to a measurement step in 1114 to determine the number of gas molecules collected by gas detector 1000. Gas detector 1000 determines the number of collected gas molecules in the same manner and using the same bias voltages as gas detector 300, except that metal grid 1010 is grounded during the measurement step.

Once the number of collected gas molecules has been determined, the method moves to an erase step in 1116 to reset gas detector 1000. Gas detector 1000 is erased by reversing the electric field for a predefined time. For example, the electric field can be reversed by electrically floating resistive structure 310, grounding p– substrate 110, and placing a large negative voltage, such as –100V, on metal grid 1010.

These bias conditions reverse the direction of the electric field which, in turn, pull the gas molecules out of resistive structure 310 and dielectric layer 312, and transport the gas molecules away from resistive structure 310. Thus, in addition to significantly enhancing the collection of gas molecules, the present invention also erases gas detector 1000.

After the predefined time, the method moves to a check step in 1118 to check the baseline current for resistive structure 310. The baseline current for resistive structure is checked by grounding substrate 110, applying the set of voltages to the opposite sides of resistive structure 310, and then measuring the current through resistive structure 310.

When the current is equal to or within an error tolerance of the baseline current associated with the set of voltages, the method returns to the collection step in 1112 to perform another test. On the other hand, when the current is greater than the error tolerance, the method returns to the calibration step in 810 to determine a new baseline current for resistive structure 310. Thus, the check step in 1118 allows the baseline current to be adjusted to account for any gas molecules that were not removed from resistive structure 310 and dielectric layer 312, thereby ensuring that the original sensitivity of gas detector 1000 is maintained.

Figure 12A:
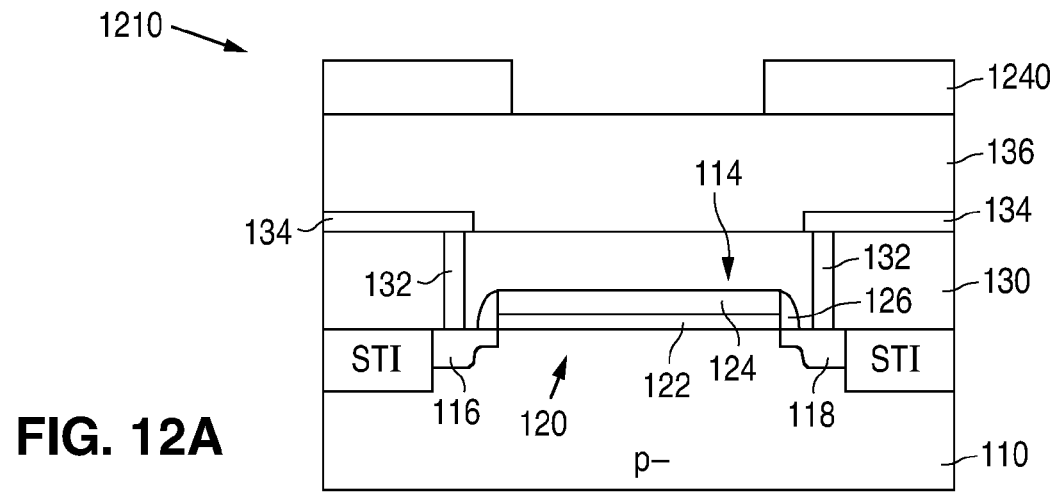
FIGS. 12A-12F are cross-sectional views illustrating a method of forming gas detector 400 in accordance with the present invention.

FIGS. 12A-12F show cross-sectional views that illustrate a method of forming gas detector 400 in accordance with the present invention. As shown in FIG. 12A, the method utilizes a conventionally-formed structure 1210. Structure 1210, in turn, is similar to gas detector 100 and, as a result, utilizes the same reference numerals to designate the elements which are common to both structures.

As further shown in FIG. 12A, the method begins by forming a patterned photoresist layer 1240 on the top surface of second dielectric layer 136. Patterned photoresist layer 1240 is formed in conventional manner, which includes depositing a layer of photoresist, projecting a light through a patterned black/clear glass plate known as a mask to form a patterned image on the layer of photoresist, which softens the photoresist regions exposed by the light, and removing the softened photoresist regions.

Figure 12B:
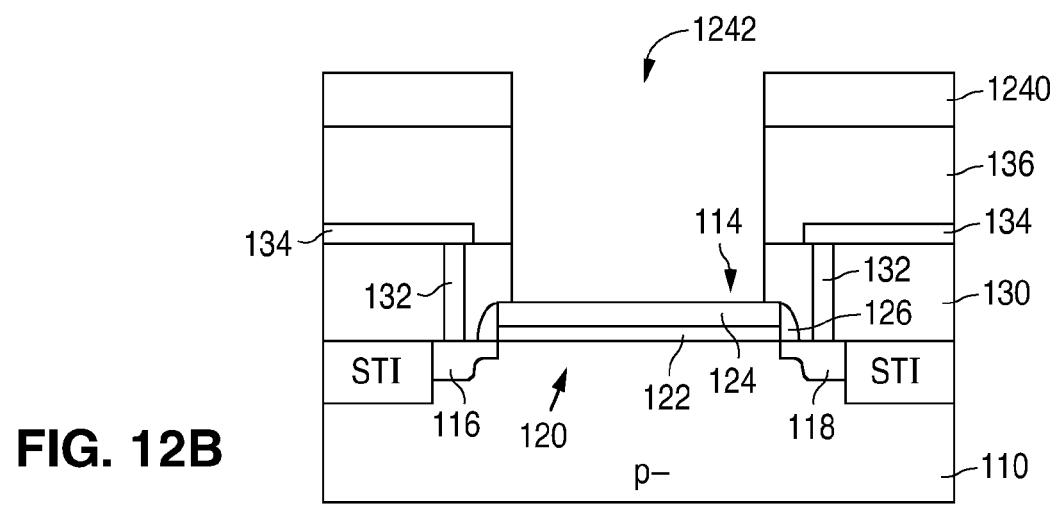

As shown in FIG. 12B, after patterned photoresist layer 1240 has been formed, the exposed regions of second dielectric layer 136 and the underlying regions of first dielectric layer 130 are etched to form a window 1242 that exposes the top surface of gate 124. Following this, patterned photoresist layer 1240 is removed.

Figure 12C:
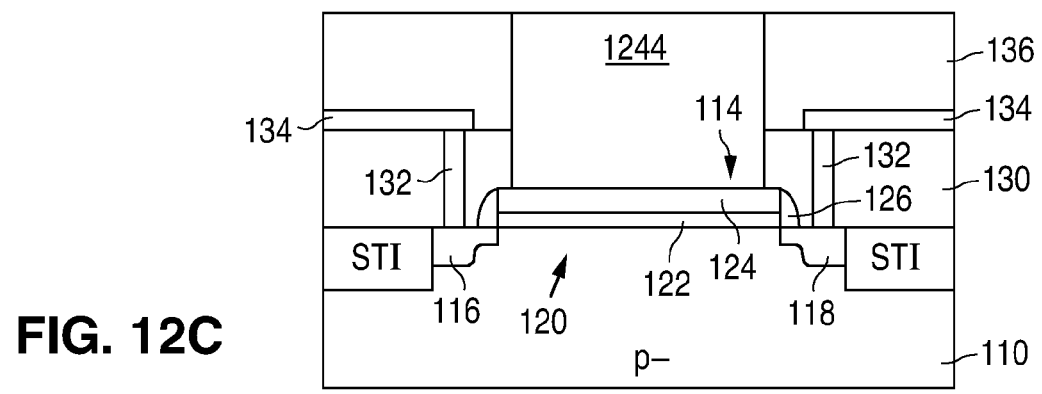

As shown in FIG. 12C, following the removal of the patterned photoresist layer 1240, a layer of sacrificial material is deposited on second dielectric layer 136 and the exposed surface of gate 124 to fill up window 1242. Once the sacrificial material has been deposited, the sacrificial material is planarized in a conventional manner to form a sacrificial region 1244.

Figure 12D:
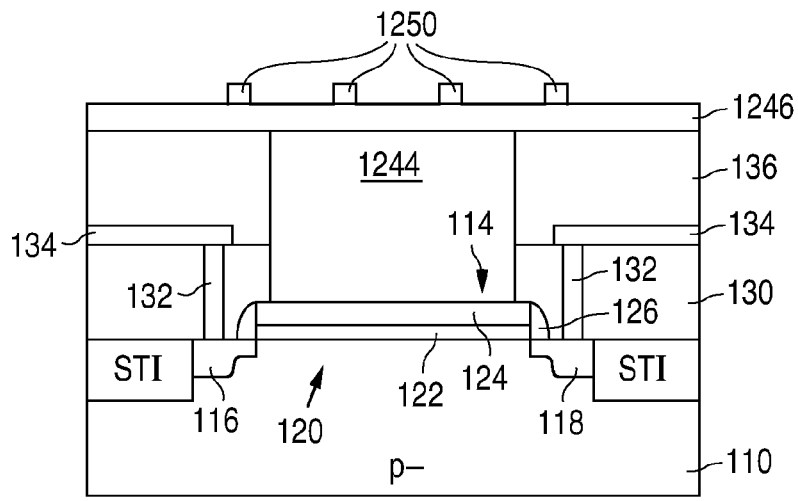
Figure 12E:
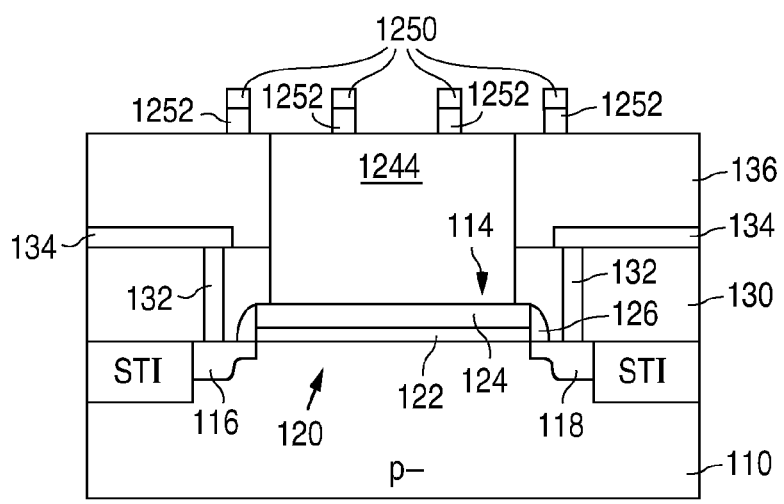
Figure 12F:
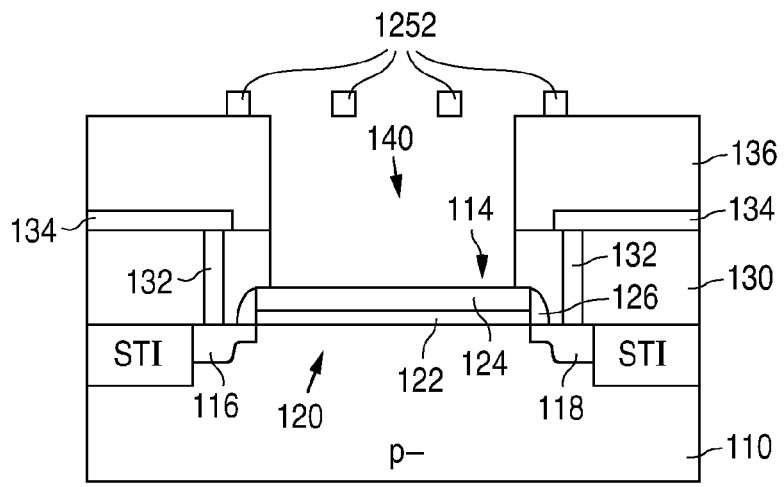

As shown in FIG. 12D, after sacrificial region 1244 has been formed, a metal layer 1246 is deposited on second dielectric layer 136 and sacrificial region 1244. Next, a patterned photoresist layer 1250 is formed on the top surface of metal layer 1246 in a conventional manner. As shown in FIG. 12E, after patterned photoresist layer 1250 has been formed, metal layer 1246 is etched to form a metal grid 1252. Following this, patterned photoresist layer 1250 is removed. As shown in FIG. 12F, following the removal of patterned photoresist layer 1250, sacrificial region 1244 is removed in a conventional manner with a wet etchant that is highly selective to second dielectric layer 136, first dielectric layer 130, and gate 124 to form gas detector 400.

Heating element 414 shown in FIGS. 4D and 4E can be formed following the conventional formation of the source and drain regions 116 and 118 of transistor 114 (which may or may not include siliciding the top surface of the source and drain regions 116 and 118). The process begins by forming isolation layer 416 on shallow trench isolation region STI, the source and drain regions 116 and 118, gate 124, and side wall spacer 126 in a conventional manner.

Next, a layer of conductive material is conventionally formed on isolation layer 416. Following this, the layer of conductive material is masked, and then etched using conventional steps to form heating element 414. After this, the process continues in a conventional manner with the formation of first dielectric layer 130.

Gas detector 600 is formed in the same manner as gas detector 400, except that structure 1210 utilizes a conventionally-formed NMOS EEPROM transistor in lieu of NMOS transistor 114. (Inter-gate dielectric 630, which can be formed before or after side wall spacer 126 has been formed, is illustrated as being formed after sidewall spacer 126 has been formed.) The floating gate of the NMOS EEPROM transistor is formed from a material that has a high permeability to the gas species to be detected. Further, heavily doped region 634 shown in FIG. 6D can be formed in a conventional manner at the same time that the source and drain regions 116 and 118 are formed.

In addition, programming gate 644 shown in FIG. 6E can be formed at the same time that control gate 632 is formed. (Conventionally, a mask is formed and patterned on a second layer of polysilicon (poly2) to define control gate 632. The mask can also be patterned to define programming gate 644 so that when the poly2 layer is etched to form control gate 632, programming gate 644 is also formed at the same time.)

Further, heavily doped region 642 shown in FIG. 6E can be formed at the same time that the source and drain regions 116 and 118 are formed. In addition, notched region 640 in gate dielectric 122 can be formed in a conventional manner, such as by masking and etching gate dielectric 122.

Heating element 650 shown in FIGS. 6F and 6G can also be formed at the same time that control gate 632 is formed. (The mask used to define control gate 632 can also be patterned to define heating element 650. Thus, when the poly2 layer is etched to form control gate 632, heating element 650 is also formed at the same time. Further, the mask can be patterned to define control gate 632, programming gate 644, and heating element 650 at the same time.)

Gas detector 1000 is also formed in the same manner as gas detector 400, except that structure 1210 utilizes a conventionally-formed resistive structure in lieu of NMOS transistor 114. The resistive structure is formed from a material that has a high permeability to the gas species to be detected.

Figure 13A:
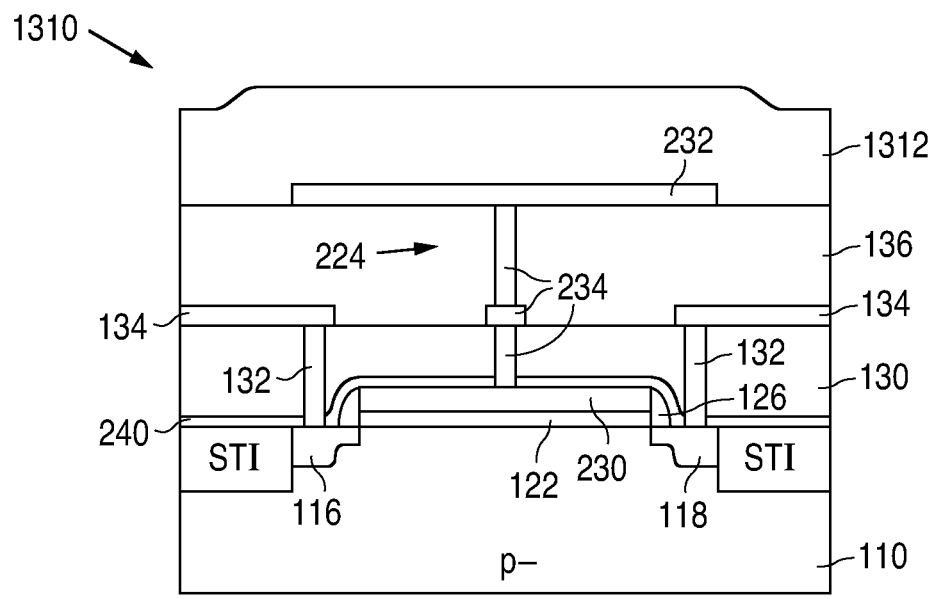
FIGS. 13A-13K are cross-sectional views illustrating a method of forming gas detector 700 in accordance with the present invention.

FIGS. 13A-13K show cross-sectional views that illustrate a method of forming gas detector 700 in accordance with the present invention. As shown in FIG. 13A, the method utilizes a conventionally-formed structure 1310. Structure 1310, in turn, is similar to gas detector 200 and, as a result, utilizes the same reference numerals to designate the elements which are common to both structures.

Figure 13B:
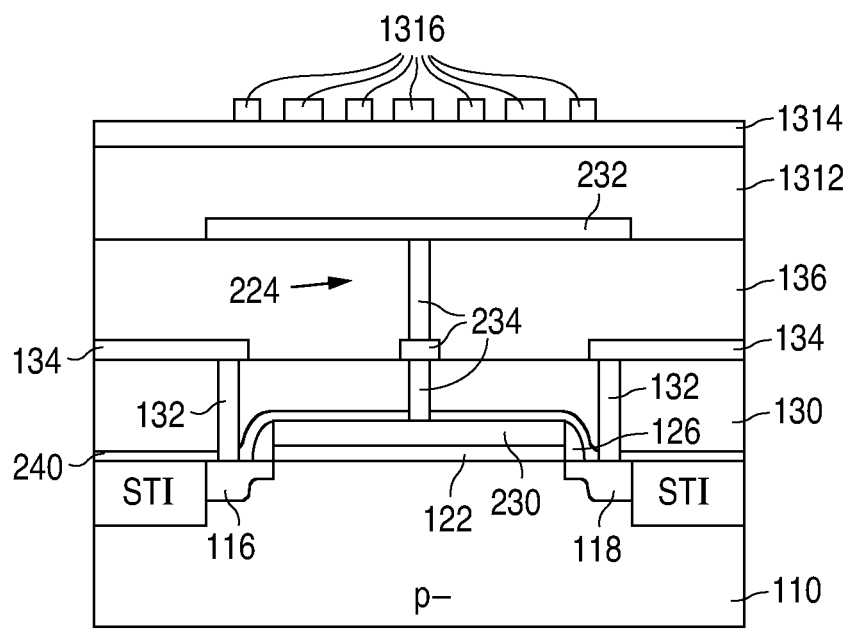

As further shown in FIG. 13A, the method begins by forming a non-conductive layer 1312 in the same manner that third dielectric layer 250 is formed, except that non-conductive layer 1312 is formed to be thicker than third dielectric layer 250. Next, as shown in FIG. 13B, non-conductive layer 1312 is planarized in a conventional manner.

Following this, a conductive layer 1314 is deposited on the top surface of non-conductive layer 1312. Conductive layer 1314 is implemented with a material that has a high permeability to the gas species to be detected. For example, lanthanum oxide, tin oxide, indium oxide, and zink oxide are materials which have a high permeability to carbon dioxide. Other materials are well known to have high permeabilities to other gas species.

Figure 13C:
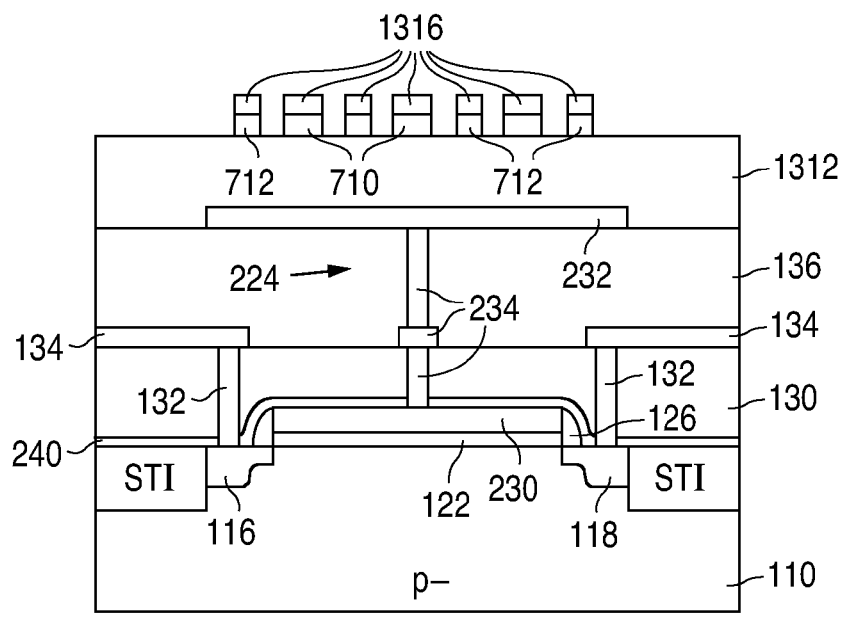
Figure 13D:
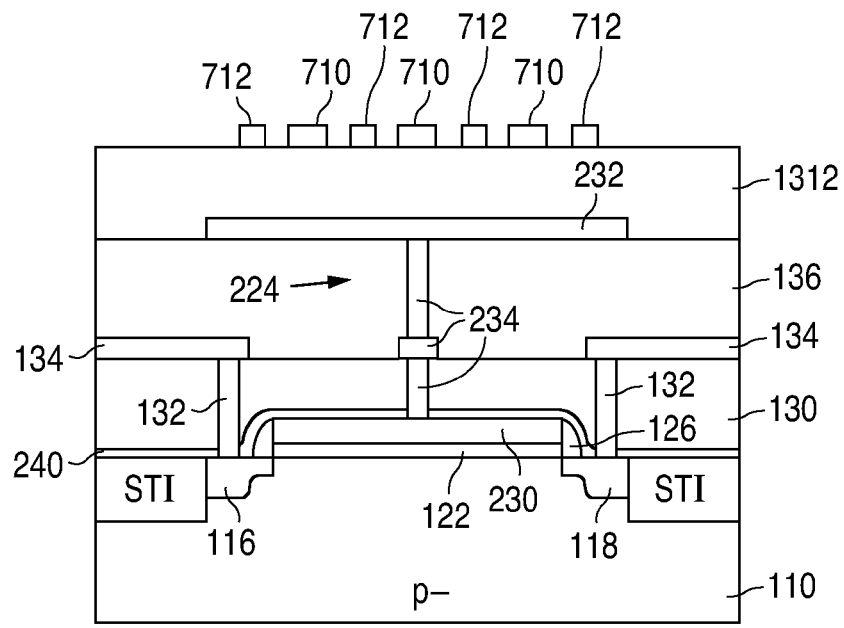

Next, a patterned photoresist layer 1316 is formed on the top surface of conductive layer 1314 in a conventional manner. As shown in FIG. 13C, after patterned photoresist layer 1316 has been formed, conductive layer 1314 is etched to form detection structure 710 and metal structure 712 shown in FIGS. 7A-7D. Following this, as shown in FIG. 13D, patterned photoresist layer 1316 is removed to form gas detector 700.

Figure 13E:
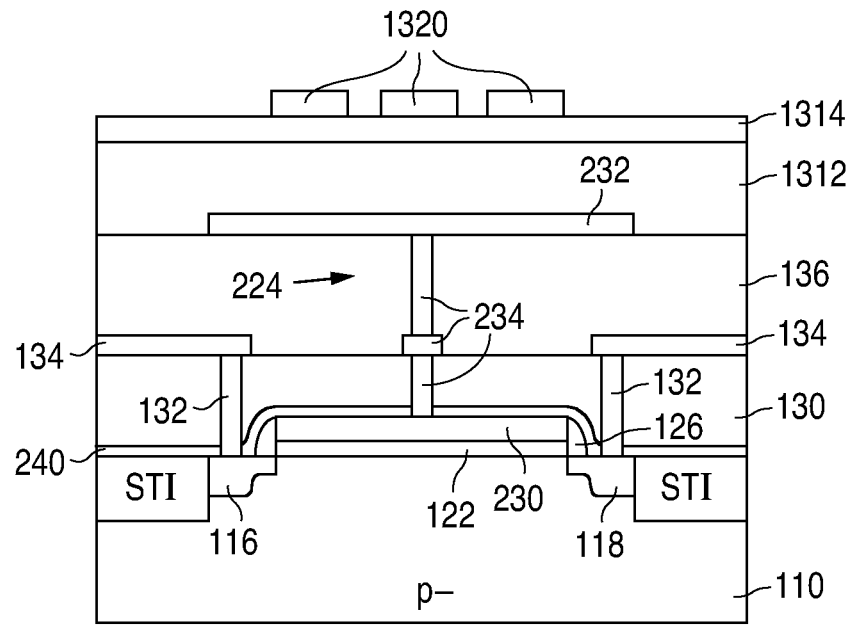
Figure 13F:
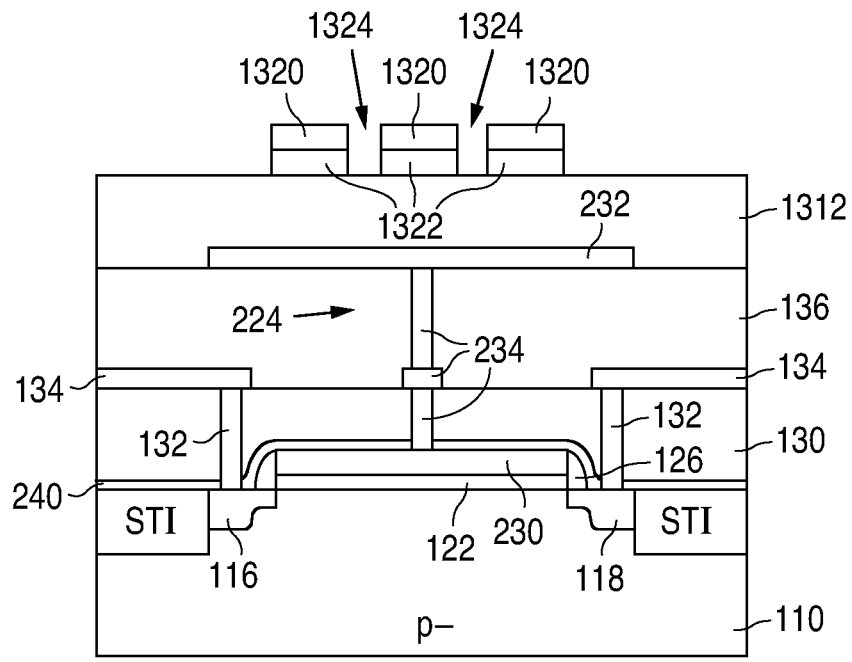
Figure 13G:
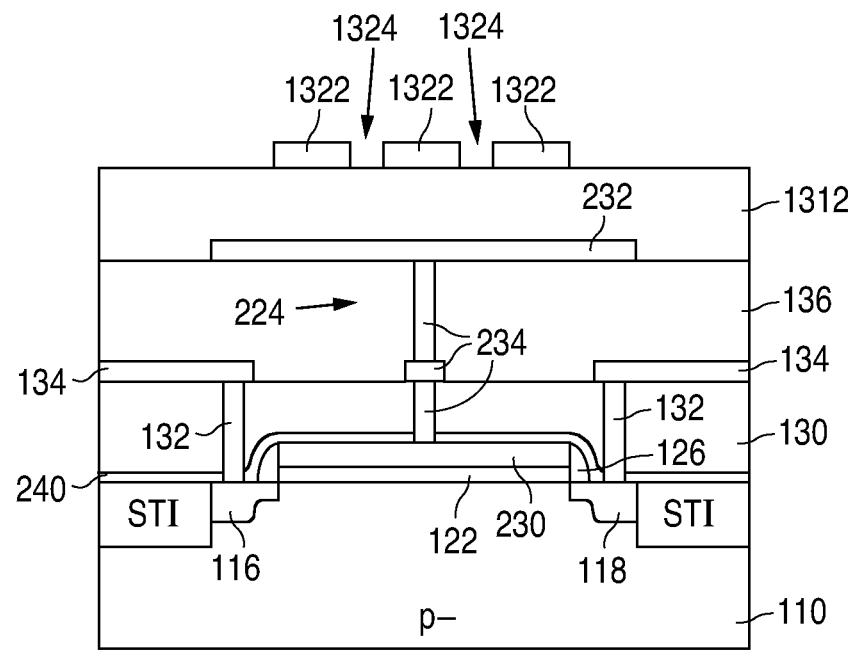
Figure 13H:
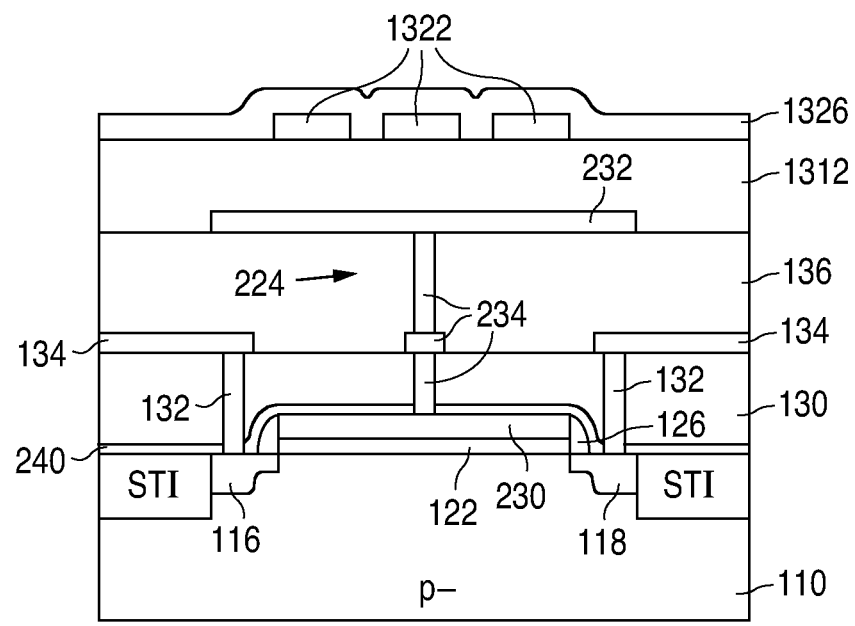
Figure 13I:
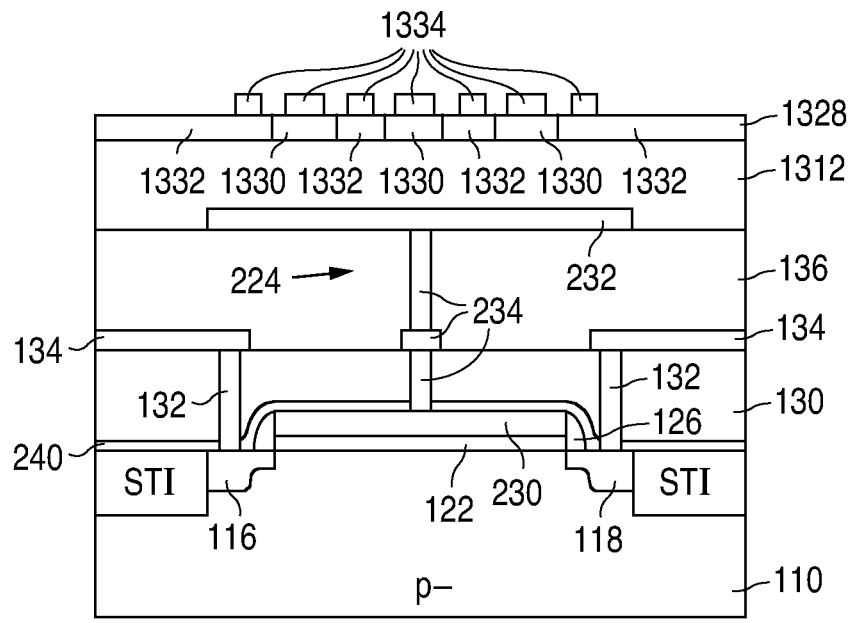

As shown in FIG. 13E, if metal structure 712 is formed from a material that has no or a very low permeability to the gas species to be detected, a patterned photoresist layer 1320 is formed on the top surface of conductive layer 1314 in a conventional manner in lieu of patterned photoresist layer 1316. As shown in FIG. 13F, after patterned photoresist layer 1320 has been formed, conductive layer 1314 is etched to form an etched layer 1322 with an opening 1324. Following this, as shown in FIG. 13G, patterned photoresist layer 1320 is removed Next, as shown in FIG. 13H, a conductive layer 1326 that has no or a very low permeability to the gas species to be detected is deposited on etched layer 1322 and non-conductive layer 1312 to fill up opening 1324. As shown in FIG. 13I, conductive layer 1326 is next planarized to remove conductive layer 1326 from the top surface of etched layer 1322 and form a conductive layer 1328 that includes a first region 1330 of high permeability material and a second region 1332 of a no or very low permeability material.

Figure 13J:
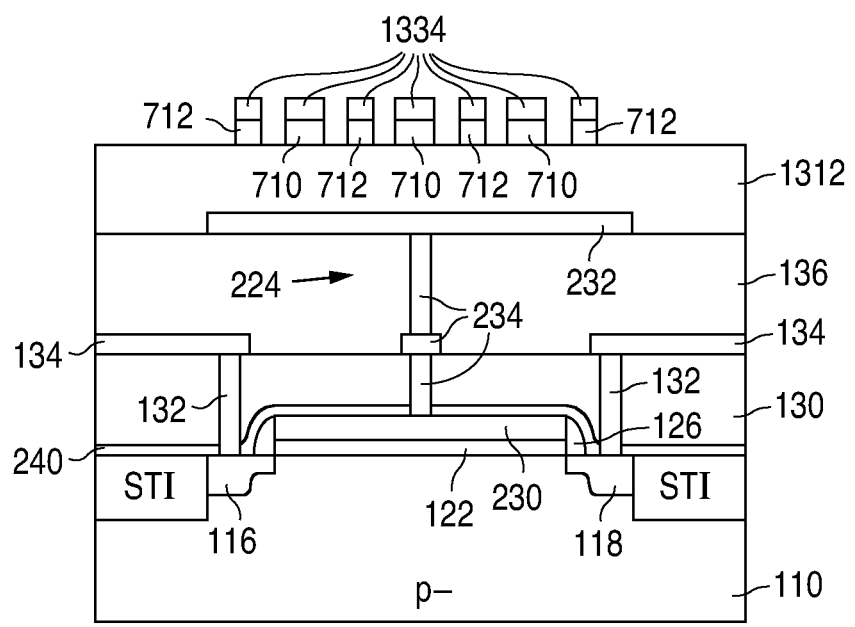
Figure 13K:
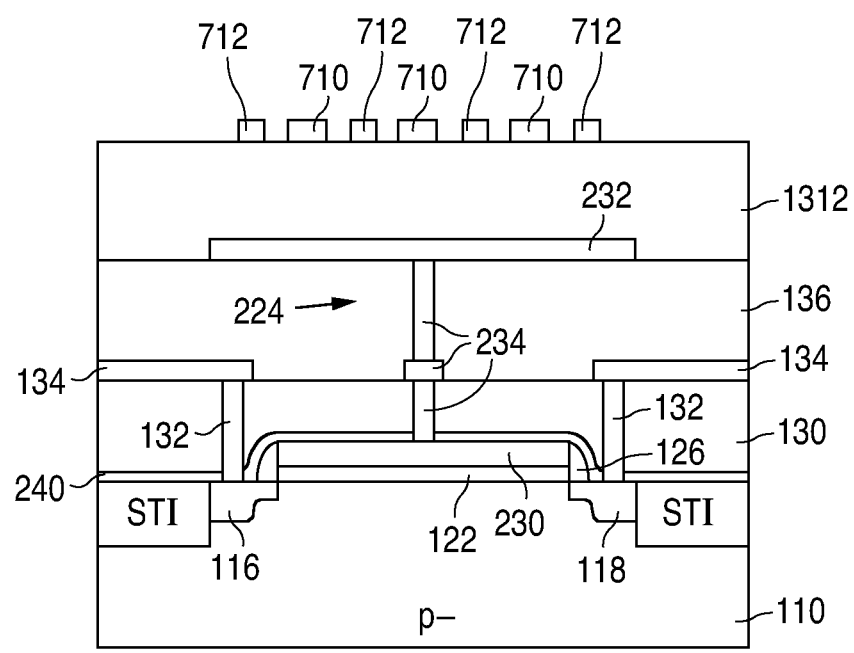

Following this, a patterned photoresist layer 1334 is formed on the top surface of conductive layer 1328 in a conventional manner. As shown in FIG. 13J, after patterned photoresist layer 1334 has been formed, conductive layer 1328 is etched to form detection structure 710 and metal structure 712 shown in FIGS. 7A-7D. Following this, as shown in FIG. 13K, patterned photoresist layer 1334 is removed to form gas detector 700.

In addition, programming gate 744 shown in FIG. 7E can be formed at the same time that control gate 242 is formed. (Conventionally, a mask is formed and patterned on a second layer of polysilicon (poly2) to define control gate 242. The mask can also be patterned to define programming gate 744 so that when the poly2 layer is etched to form control gate 242, programming gate 744 is also formed at the same time.)

Further, heavily doped region 742 shown in FIG. 7E can be formed at the same time that the source and drain regions 116 and 118 are formed. In addition, notched region 740 in gate dielectric 122 can be formed in a conventional manner, such as by masking and etching gate dielectric 122. Gas detector 900 is formed in the same manner as illustrated in FIGS. 13A-13K, except that the steps illustrated in FIGS. 13A-13K are also utilized to form metal structures 930 and 932.

Thus, gas detectors in accordance with the present invention have been described which utilize metal structures to set up electric fields that substantially enhance the collection of gas molecules, and also provide a self contained means for removing collected gas molecules from the gas detector.

In addition, methods of operating the gas detectors have been described. In steps 510, 810 and 1110, the methods determine a magnitude of a current, such as a drain-to-source current and a resistor current, to define a first current magnitude. After the first current magnitude has been defined, in steps 512, 812, and 1112, the methods set up an electric field to transport gas molecules to a detection structure, such as gate 124 of gas detector 400, floating gate 624 of gas detector 600, detection structure 710 of gas detectors 700 and 900, and resistive structure 310 of gas detector 1000.

Following this, in steps 514, 814, and 1114, the methods remove the electric field after a predetermined period of time, and determine the magnitude of the current to define a second current magnitude. The methods determine that gas molecules were transported to the detection structure during the predetermined period of time if a difference between the second current magnitude and the first current magnitude is greater than an error tolerance. As described above, the difference is used to then determine the concentration of the gas species.

After this, in steps 516, 816, and 1116, the methods set up a reverse electric field to transport gas molecules away from the detection structure for a predefined time, and then remove the electric field after the predefined time. Once the reverse electric field has been removed, in steps 518, 818, and 1118, the methods determine the magnitude of the current to define a third current magnitude.

When the difference between the third current magnitude and the first current magnitude is greater than an error tolerance, the methods return to step 510, 810 and 1110 to determine the magnitude of the current to redefine the first current magnitude. When the difference between the third current magnitude and the first current magnitude is less than the error tolerance, the methods return to step 512, 812 and 1112 to perform another test.

It should be understood that the above descriptions are examples of the present invention, and that various alternatives of the invention described herein may be employed in practicing the invention. Thus, it is intended that the following claims define the scope of the invention and that structures and methods within the scope of these claims and their equivalents be covered thereby.

What is claimed is:

1. A method of operating a gas detector comprising:
   determining a magnitude of a current to define a first current magnitude;
   setting up an electric field to transport gas molecules to a detection structure after the first current magnitude has been defined;
   removing the electric field after a predetermined period of time;
   determining the magnitude of the current to define a second current magnitude after the electric field has been removed, a difference between the second current magnitude and the first current magnitude being greater than an error tolerance if gas molecules were transported to the detection structure;
   further comprising setting up a reverse electric field to transport gas molecules away from the detection structure;
   removing the reverse electric field after a predefined period of time;
   determining the magnitude of the current to define a third current magnitude after the reverse electric field has been removed; and
   further comprising determining the magnitude of the current to redefine the first current magnitude when a difference between the third current magnitude and the first current magnitude is greater than an error tolerance.

2. The method of claim 1 wherein the current flows from a first doped region of a first conductivity type to a second doped region of the first conductivity type through a semiconductor material of a second conductivity type.

3. The method of claim 1 wherein the current flows through the detection structure.

4. The method of claim 1 wherein the electric field extends vertically from a metal structure that lies above the detection structure to a semiconductor material that lies below the detection structure, the semiconductor material having a conductivity type.

5. The method of claim 4 wherein the detection structure is separated from the semiconductor material by a dielectric layer, the dielectric layer touching the detection structure and the semiconductor material.

6. The method of claim 1 wherein an electric field extends vertically from a metal structure to a floating gate structure.

7. The method of claim 1 wherein the electric field extends horizontally from a metal structure to the detection structure.

8. The method of claim 7 wherein an air gap lies horizontally between the metal structure and the detection structure.

9. The method of claim 8 wherein the detection structure is separated from a floating gate structure that lies vertically below the detection structure by a dielectric structure.

10. The method of claim 1 wherein the detection structure has a high permeability to a gas species.

11. The method of claim 1 wherein the detection structure is electrically isolated from all other conductive structures.

12. A gas detector comprising:

a dielectric structure;

a detection structure that touches the dielectric structure, the detection structure having a high permeability to a gas species; and a metal structure that touches the dielectric structure;

a semiconductor material, the semiconductor material having a conductivity type;

a dielectric layer that touches a top surface of the semiconductor material, the detection structure touching a top surface of the dielectric layer; and an opening in the dielectric structure that exposes a top surface of the detection structure, the metal structure extending across a top of the opening without closing the opening.

13. A method of forming a gas detector comprising:

forming a detection structure that has a high permeability to a gas species;

forming a dielectric structure that touches the detection structure;

forming a metal structure that touches the dielectric structure;

forming a semiconductor material, the semiconductor material having a conductivity type;

forming a dielectric layer that touches a top surface of the semiconductor material, the detection structure touching a top surface of the dielectric layer; and forming an opening in the dielectric structure that exposes a top surface of the detection structure, the metal structure extending across a top of the opening without closing the opening.

* * * * *